US009943502B2

(12) United States Patent
Gao

(10) Patent No.: US 9,943,502 B2
(45) Date of Patent: Apr. 17, 2018

(54) LUNG CANCER ADJUVANT THERAPY

(71) Applicant: Texas Tech University System, Lubbock, TX (US)

(72) Inventor: Weimin Gao, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/313,339

(22) PCT Filed: May 27, 2015

(86) PCT No.: PCT/US2015/032714
§ 371 (c)(1),
(2) Date: Nov. 22, 2016

(87) PCT Pub. No.: WO2015/183983
PCT Pub. Date: Dec. 3, 2015

(65) Prior Publication Data
US 2017/0196836 A1 Jul. 13, 2017

Related U.S. Application Data

(60) Provisional application No. 62/004,634, filed on May 29, 2014.

(51) Int. Cl.
*A61K 31/335* (2006.01)
*A61K 31/35* (2006.01)
*A61K 31/28* (2006.01)
*A61K 31/215* (2006.01)
*A61K 31/12* (2006.01)
*A61K 31/366* (2006.01)
*A61K 33/24* (2006.01)
*C12Q 1/68* (2018.01)
*G01N 33/574* (2006.01)
*C12N 15/113* (2010.01)

(52) U.S. Cl.
CPC ........... *A61K 31/366* (2013.01); *A61K 33/24* (2013.01); *C12N 15/113* (2013.01); *C12Q 1/6886* (2013.01); *G01N 33/574* (2013.01); *G01N 33/57423* (2013.01); *G01N 33/57496* (2013.01); *C12N 2310/14* (2013.01); *C12N 2310/531* (2013.01); *C12N 2320/31* (2013.01); *C12Q 2600/106* (2013.01); *C12Q 2600/158* (2013.01); *G01N 2333/47* (2013.01); *G01N 2333/4748* (2013.01); *G01N 2440/14* (2013.01)

(58) Field of Classification Search
CPC ...... A61K 31/337; A61K 31/35; A61K 31/28; A61K 8/671; A61K 31/12
USPC .......... 514/449, 460, 492, 529, 678
See application file for complete search history.

(56) References Cited

U.S. PATENT DOCUMENTS 8,048,888 B2 11/2011 Wosikowski-Butters et al.
8,580,792 B2 11/2013 Danter
2005/0203174 A1 9/2005 Santi et al.

OTHER PUBLICATIONS

Liu, L., et al. "Rapamycin inhibits cytoskeleton reorganization and cell motility by suppressing RhoA expression and activity." J Biol Chem, Dec. 3, 2010. 285(49): p. 38362-73.
Lo, H.W., et al. "Nuclear-cytoplasmic transport of EGFR involves receptor endocytosis, importin beta1 and CRM1." J Cell Biochem, 2006. 98(6): p. 1570-83.
Lobo, V., et al. "Free radicals, antioxidants and functional foods: Impact on human health." Pharmacogn Rev, Jul.-Dec. 2010. 4(8): p. 118-26.
Lowenstein, E.J., et al. "The SH2 and SH3 domain-containing protein GRB2 links receptor tyrosine kinases to ras signaling." Cell, Aug. 7, 1992. 70(3): p. 431-42.
Lu, C., et al. "Chemotherapeutic sensitization of leptomycin B resistant lung cancer cells by pretreatment with doxorubicin." PLoS One, Mar. 7, 2012. 7(3): p. e32895.
McVean, M., et al. "Increase in wild-type p53 stability and transactivational activity by the chemopreventive agent apigenin in keratinocytes." Carcinogenesis, 2000. 21(4): p. 633-9.
Meek, D.W. "Multisite phosphorylation and the integration of stress signals at p53." Cell Signal, 1998. 10(3): p. 159-66.
Moss, S.C., et al. "Rapamycin regulates endothelial cell migration through regulation of the cyclin-dependent kinase Inhibitor p27Kip1." J Biol Chem, Apr. 16, 2010. 285(16): p. 11991-7.
Mutka, S.C., et al. "Identification of nuclear export inhibitors with potent anticancer activity in vivo." Cancer Res, Jan. 15, 2009. 69(2): p. 510-7.
Newlands, E.S. et al. "Phase I trial of elactocin." Br J Cancer, Mar. 1996. 74(4): p. 648-9.
Nigro, J.M., et al. "Mutations in the p53 gene occur in diverse human tumour types." Nature, Dec. 7, 1989. 342(6250): p. 705-708.
Noske, A., et al. "Expression of the nuclear export protein chromosomal region maintenance/exportin 1/Xpo1 is a prognostic factor in human ovarian cancer." Cancer, Feb. 27, 2008. 112(8): p. 1733-43.
Ranganathan P, et al. "Pre-clinical activity of a novel CRM1 inhibitor in acute myeloid leukemia." Blood, Aug. 30, 2012: 120(9) p. 1765-1773.
Rhodes, N. et al. "Molecular mechanisms of environmental carcinogenesis." Environ Health Perspect, May 1995. 103(5): p. 504-6.
Rodriguez, M.S. et al. "Nuclear export of RNA." Biol Cell, Aug. 3, 2004. 96(8): p. 639-55.
Ryan, K.M., et al. "Regulation and function of the p53 tumor suppressor protein." Current Opinion in Cell Biology, 2001. 13(3): p. 332-337.
Sakakibara, K., et al. "CBS9106 is a novel reversible oral CRM1 inhibitor with CRM1 degrading activity." Blood, Oct. 6, 2011. 118(14): p. 3922-31.

(Continued)

*Primary Examiner* — Raymond J Henley, III
(74) *Attorney, Agent, or Firm* — Edwin S. Flores; Daniel J. Chalker; Chalker Flores, LLP

(57) ABSTRACT

The present invention includes compositions and methods for the treatment of cancer comprising an antineoplastic drug and an inhibitor of chromosome maintenance region 1 (CRM1) protein expression or activity, wherein the inhibitor of CRM1 enhances the anti-neoplastic effect of the antineoplastic drug.

36 Claims, 7 Drawing Sheets

(56) References Cited

OTHER PUBLICATIONS

Schlamp, C.L., et al. "Nuclear exclusion of wild-type p53 in immortalized human retinoblastoma cells." Journal of the National Cancer Institute, Oct. 15, 1997. 89(20): p. 1530-1536.

Schreiber, V., et al. "Poly (ADP-ribose): novel functions for an old molecule." Nature Reviews Molecular Cell Biology, Jul. 2006. 7(7): p. 517-528.

Schwartz, A.G., et al. "The molecular epidemiology of lung cancer." Carcinogenesis, 2007. 28(3): p. 507-18.

Scoumanne, A. et al. "Protein methylation: a new mechanism of p53 tumor suppressor regulation." Histology and Histopathology, Sep. 2008. 23(9): p. 1143-1149.

Shao, C., et al. "p53-Dependent anticancer effects of leptomycin B on lung adenocarcinoma." Cancer Chemother Pharmacol, 2011. 67(6): p. 1369-80.

Shim, J., et al. "Nuclear export of NF90 is required for interleukin-2 mRNA stabilization." Mol Cell, Dec. 2002. 10 6): p. 1331-44.

Sozzi, G., et al. "Genetic evidence for an independent origin of multiple preneoplastic and neoplastic lung lesions." Cancer Res, Jan. 1, 1995. 55(1): p. 135-40.

Stabile, L.P., et al. "Therapeutic targeting of human hepatocyte growth factor with a single neutralizing monoclonal antibody reduces lung tumorigenesis." Mol Cancer Ther, Jul. 2008. 7(7): p. 1913-22.

Stabile, L.P., et al. "Transgenic mice overexpressing hepatocyte growth factor in the airways show increased susceptibility to lung cancer." Carcinogenesis, 2006. 27(8): p. 1547-55.

Stauber, R.H. et al. "Nuclear and cytoplasmic survivin: molecular mechanism, prognostic, and therapeutic potential." Cancer Res, Jul. 1, 2007. 67(13): p. 5999-6002.

Stenmarkaskmalm, M., et al. "Cellular Accumulation of P53 Protein—an Independent Prognostic Factor in Stage-li Breast-Cancer." European Journal of Cancer, 1994. 30A(2): p. 175-180.

Stommel, J.M., et al. "A leucine-rich nuclear export signal in the p53 tetramerization domain: regulation of subcellular localization and p53 activity by NES masking." Embo J, 1999. 18(6): p. 1660-72.

Sun, X.F., et al. "Prognostic-Significance of Cytoplasmic-P53 Oncoprotein in Colorectal Adenocarcinoma." Lancet, Dec. 5, 1992. 340(8832): p. 1369-1373.

Touge, H., et al. "Diverse activation states of RhoA in human lung cancer cells: contribution of G protein coupled receptors." Int J Oncol, 2007. 30(3): p. 709-15.

Turner, J.G.et al. "CRM1-Mediated Nuclear Export of Proteins and Drug Resistance in Cancer." Current Medicinal chemistry, 2008. 15(26): p. 2648-2655.

Turner, J.G. et al. "Nuclear export of proteins and drug resistance in cancer." Biochem Pharmacol, Apr. 15, 2012. 83(8): p. 1021-32.

Uldrijan, S. et al. "Regulation of the p53 tumour suppressor stability and activity." Chemicke Listy, 2002. 96(3): p. 145-149. [Abstract—English].

van der Watt, P.J. et al. "The nuclear exporter, Crm1, is regulated by NFY and Sp1 in cancer cells and repressed by p53 in response to DNA damage." Biochim Biophys Acta, Jun. 13, 2011. 1809(7): p. 316-26.

van der Watt, P.J., et al. "The Karyopherin proteins, Crm1 and Karyopherin beta1, are overexpressed in cervical cancer and are critical for cancer cell survival and proliferation." Int J Cancer, 2008. 124(8): p. 1829-1840.

Walker, K.K. "Identification of a novel p53 functional domain that is necessary for efficient growth suppression." Proc Natl Acad Sci U S A, Dec. 1996. 93(26): p. 15335-40.

Wingo, P.A., et al. "Annual report to the nation on the status of cancer, 1973-1996, with a special section on lung cancer and tobacco smoking." J Natl Cancer Inst, Apr. 21, 1999. 91(8): p. 675-90.

Wogan, G.N., et al. "Environmental and chemical carcinogenesis." Seminars in Cancer Biology, 2004. 14(6): p. 173-486.

Wu, Y.K., et al. "Quantitative detection of survivin in malignant pleural effusion for the diagnosis and prognosis of lung cancer." Cancer Lett, 2009. 273(2): p. 331-5.

Xu, L. et al. "Nucleocytoplasmic shuttling of signal transducers." Nat Rev Mol Cell Biol, Mar. 2004. 5(3): p. 209-19.

Yao, Y., et al. "The expression of CRM1 is associated with prognosis in human osteosarcoma." Oncol Rep, 2009. 21(1): p. 229-35.

Yoshioka, K. et al. "Overexpression of small GTP-binding protein RhoA promotes invasion of tumor cells." Cancer Res, Apr. 15, 1999. 59(8): p. 2004-10.

Zerfaoui, M., et al. "Poly(ADP-ribose) polymerase-1 is a determining factor in Crm1-mediated nuclear export and retention of p65 NF-kappa B upon TLR4 stimulation." J Immunol, 2010. 185(3): p. 1894-902.

Zhu, J., et al."Identification of a novel p53 functional domain that is necessary for mediating apoptosis." J Biol Chem, May 22, 1998. 273(21): p. 13030-6.

Zhu, W., et al. "Curcumin and Vitamin E Protect against Adverse Effects of Benzo[a]pyrene in Lung Epithelial Cells." PLoS One, Mar. 24, 2014. 9(3): p. e92992.

Adachi, Y. et al. "Higher order chromosome structure is affected by cold-sensitive mutations in a Schizosaccharomyces pombe gene crm1+ which encodes a 115-kD protein preferentially localized in the nucleus and its periphery." J Cell Biol, Apr. 1989. 108(4): p. 1195-207.

Behera, D., "Managing lung cancer in developing countries: difficulties and solutions." Indian J Chest Dis Allied Sci, 2006. 48(4): p. 243-4.

Boyle, J.O., et al., "Cyclin D1 proteolysis: a retinoid chemoprevention signal in normal, immortalized, and transformed human bronchial epithelial cells." J Natl Cancer Inst, Feb. 17, 1999. 91(4): p. 373-9.

Cai, X.et al. "Inhibition of Thr-55 phosphorylation restores p53 nuclear localization and sensitizes cancer cells to DNA damage." Proc Natl Acad Sci USA, Nov. 4, 2008. 105(44): p. 16958-63.

Carbone, D., "Smoking and cancer." Am J Med, Jul. 15, 1992. 93(1A): p. 13S-17S.

Chen, L et al. "4-(methylnitrosamino)-1-(3-pyridyl)-1-butanone [corrected] induces CRM1-dependent p53 nuclear accumulation in human bronchial epithelial cells." Toxicol Sci, Apr. 26, 2010. 116(1): p. 206-15.

Chen, L, et al., "CRM1-dependent p53 nuclear accumulation in lung lesions of a bitransgenic mouse lung tumor model." Oncol Rep, 2011.26(1): p. 223-8.

Chuikov, S., et al., "Regulation of p53 activity through lysine methylation." Nature, Nov. 18, 2004. 432(7015): p. 353-360.

Cook, A., et al., "Structural biology of nucleocytoplasmic transport." Annu Rev Biochem, 2007. 76: p. 647-71.

Cullen, B.R., "Nuclear RNA export." J Cell Sci, 2001 116(Pt 4): p. 587-97.

del Peso, L., et al., Rho proteins induce metastatic properties in vivo. Oncogene, 1997. 15(25): p. 3047-57.

Devesa, S.S., et al., International lung cancer trends by histologic type: male:female differences diminishing and adenocarcinoma rates rising. Int J Cancer, 2005. 117(2): p. 294-9.

el-Deiry, W.S., et al. "WAF1, a potential mediator of p53 tumor suppression." Cell, Nov. 19, 1993. 75(4): p. 817-25.

Etienne-Manneville, S. et al. "Rho GTPases in cell biology." Nature, Dec. 12, 2002. 420(6916): p. 629-35.

Foo, R.S., et al., "Regulation of p53 tetramerization and nuclear export by ARC." Proc Natl Acad Sci USA, Dec. 26, 2007. 104(52): p. 20826-31.

Freedman, N. D., et al. "Cigarette smoking and subsequent risk of lung cancer in men and women: analysis of a prospective cohort study." Lancet Oncology, Jul. 2008. 9(7): p. 649-656.

Fried, H. et al. "Nucleocytoplasmic transport: taking an inventory." Cell Mol Life Sci, 2003. 60(8): p. 1659-88.

Fritz, G. et al. "Rho GTPases are over-expressed in human tumors." Int J Cancer, 1999. 81(5): p. 682-7.

Gademann, K. "Controlling protein transport by small molecules." Curr Drug Targets, 2011. 12(11): p. 1574-80.

Galluzzi, L., et al. "Molecular mechanisms of cisplatin resistance." Oncogene, 2012. 31(15): p. 1869-83.

(56) References Cited

OTHER PUBLICATIONS

Gao, W.M., et al. "Analysis of p53 mutations in histologically normal lung tissues and lung tumors from non-small cell lung cancer patients." Mol Carcinog, 2009. 48(7): p. 633-641.

Gao, W.M., et al. "Association of the DNA repair gene XPD Asp312Asn polymorphism with p53 gene mutations in tobacco-related non-small cell lung cancer." Carcinogenesis, 2003. 24(10): p. 1671-6.

Gao, W.M., et al. "Comparison of p53 mutations between adenocarcinoma and squamous cell carcinoma of the lung: unique spectra involving G to A transitions and G to T transversions in both histologic types." Lung Cancer, 2003. 40(2): p. 141-50.

Garcia, M., et al. "Global Cancer Facts & Figures 2007." 2007, Atlanta, GA: American Cancer Society. 1-50.

Gulhati, P., et al. "mTORC1 and mTORC2 regulate EMT, motility, and metastasis of colorectal cancer via RhoA and Rac1 signaling pathways." Cancer Res, May 1, 2011. 71(9): p. 3246-56.

Harrison, B.C., et al. "The CRM1 nuclear export receptor controls pathological cardiac gene expression." Mol Cell Biol, Dec. 2004. 24(24): p. 10636-49.

Hecht, S.S. "Biochemistry, biology, and carcinogenicity of tobacco-specific N-nitrosamines." Chemical Research in Toxicology, Jun. 1998. 11(6): p. 559-603.

Hecht, S.S. "Carcinogenicity studies of inhaled cigarette smoke in laboratory animals: old and new." Carcinogenesis, 2005. 26(9): p. 1488-92.

Hecht, S.S. "Cigarette smoking and lung cancer: chemical mechanisms and approaches to prevention." Lancet Oncology, Aug. 2002. 3(8): p. 461-469.

Hecht, S.S. "Progress and challenges in selected areas of tobacco carcinogenesis." Chemical Research in Toxicology, Jan. 2008. 21(1): p. 160-171.

Hecht, S.S. "Recent studies on mechanisms of bioactivation and detoxification of 4-(methylnitrosamino)-1-(3-pyridyl)-1-butanone (NNK), a tobacco-specific lung carcinogen." Critical Reviews in Toxicology, 1996. 26(2): p. 163-181.

Hecht, S.S. "Tobacco smoke carcinogens and lung cancer." Journal of the National Cancer Institute, Jul. 21, 1999. 91(14): p. 1194-1210.

Herold, A. et al."Genome-wide analysis of nuclear mRNA export pathways in *Drosophila*." EMBO J, 2003. 22(10): p. 2472-83.

Hsu, S.-C., et al. "Nuclear EGFR is required for cisplatin resistance and DNA repair." American journal of translational research, 2009. 1(3): p. 249.

Huang, W.Y., et al. "Prognostic value of CRM1 in pancreas cancer." Clin Invest Med, Dec. 2009. 32(6): p. E315.

Jacinto, E., et al. "Mammalian TOR complex 2 controls the actin cytoskeleton and is rapamycin insensitive." Nat Cell Biol, Nov. 2004. 6(11): p. 1122-8.

Jang, B.C., et al. "Leptomycin B, an inhibitor of the nuclear export receptor CRM1, inhibits COX-2 expression." J Biol Chem, Jan. 31, 2003. 278(5): p. 2773-6.

Jemal, A., et al. "Cancer statistics, 2009." CA Cancer J Clin, Jul./Aug. 2009. 59(4): p. 225-49.

Jimenez, G.S., et al. "p53 regulation by post-translational modification and nuclear retention in response to diverse stresses." Oncogene, 1999. 18(53): p. 7656-7665.

Kaden, D.A. et al. "Mutagenicity of soot and associated polycyclic aromatic hydrocarbons to *Salmonella typhimurium*." cancer Res, Oct. 1979. 39(10): p. 4152-9.

Kamai, T., et al. "RhoA is associated with invasion and lymph node metastasis in upper urinary tract cancer." BJU Int, 2003. 91(3): p. 234-8.

Kanai, M., et al. "Inhibition of Crm1-p53 interaction and nuclear export of p53 by poly(ADP-ribosyl)ation." Nat Cell Biol, Oct. 2007. 9(10): p. 1175-83.

Keohavong, P., et al. "Detection of p53 and K-ras mutations in sputum of individuals exposed to smoky coal emissions in Xuan Wei County, China." Carcinogenesis, 2005. 26(2): p. 303-8.

Keohavong, P., et al. "Topographic analysis of K- ras mutations in histologically normal lung tissues and tumours of lung cancer patients." Br J Cancer, 2001. 85(2): p. 235-41.

Kleine, H., et al. "Dynamic subcellular localization of the mono-ADP-ribosyltransferase ARTD10 and interaction with the ubiquitin receptor p62." Cell Commun Signal, 2012. 10(1): p. 28.

Komiyama, K., et al. "Antitumor activity of leptomycin B. J Antibiot" (Tokyo), Mar. 1985. 38(3): p. 427-9.

Kudo, N., et al. "Leptomycin B inactivates CRM1/exportin 1 by covalent modification at a cysteine residue in the central conserved region." Proc Natl Acad Sci USA, Aug. 1999. 96(16): p. 9112-7.

Kudo, N., et al. "Molecular cloning and cell cycle-dependent expression of mammalian CRM1, a protein involved in nuclear export of proteins." J Biol Chem, Nov. 21, 1997. 272(47): p. 29742-51.

Lin, C.C., et al. "Inhibition of basal FGF receptor signaling by dimeric Grb2." Cell, Jun. 22, 2012. 149(7): p. 1514-24.

Lin, M.T., et al. "Cyclooxygenase-2 inducing Mcl-1-dependent survival mechanism in human lung adenocarcinoma CL1.0 cells. Involvement of phosphatidylinositol 3-kinase/Akt pathway." J Biol Chem, Dec. 28, 2001. 276(52): p. 18997-9002.

LUNG CANCER ADJUVANT THERAPY

CROSS-REFERENCE TO RELATED APPLICATIONS

This application claims priority to, and is a National Stage Patent Application of International Application No. PCT/US2015/032714 filed on May 27, 2015, which claims priority to U.S. Provisional Patent Application Ser. No. 62/004,634, filed on May 29, 2014. The contents of both applications are incorporated by reference herein in their entirety.

TECHNICAL FIELD OF THE INVENTION

The present invention relates in general to the field of treatments for lung cancer, and more particularly, to a novel lung cancer adjuvant therapy.

REFERENCE TO A SEQUENCE LISTING

The present application includes a Sequence Listing which has been submitted in ASCII format via EFS-Web and is hereby incorporated by reference in its entirety. Said ASCII copy, created on May 26, 2015, is named TECH2079WO_SL.txt and is 1 KB in size.

BACKGROUND OF THE INVENTION

Without limiting the scope of the invention, its background is described in connection with treatments for lung cancer.

U.S. Pat. No. 8,580,792, issued to Danter is directed to inhibitor compounds and cancer treatment methods. Specifically, this patent is said to teach the a synergistically effective combination of an anti-cancer agent and a therapeutic compound, such as an mTOR-Rictor complex inhibitor, a Serine 473 phosphorylation inhibitor, an AKT2 inhibitor, or a combination thereof, for use in the treatment of cancer, and methods and uses thereof Also included are methods and uses of a thiosemicarbazone compound for treating a cancer in a mammal in need thereof characterized by over-expression of RAS, by an EGFR mutation, and/or by over-expression of AKT2.

U.S. Pat. No. 8,048,888, issued to Wosikowski-Buters, et al., is directed to an anti-proliferative combination therapy using certain platinum-based chemotherapeutic agents and EGFR inhibitors or pyrimidine analogues. Briefly, this patent is said to teach a method or uses of prevention and/or treatment of a cancer or a tumor, and in particular to a combination therapy, methods, compositions and pharmaceutical packages comprising an inhibitor of receptors of the EGFR family or a chemotherapeutically active pyrimidine analogue and certain platinum-based chemotherapeutic agents.

United States Patent Application Publication No. 2005/0203174, filed by Santi, et al., is directed to combination therapies using leptomycin B. Briefly, these applicants teach that cellular proliferation in colon cancers can be treated with a combination of leptomycin B and a chemotherapeutic co-agent, for instance an anti-mitotic agent, a DNA cleaver, an alkylating agent, a DNA crosslinking agent, a DNA intercalator, an HSP90 inhibitor, a topoisomerase I inhibitor, a topoisomerase II inhibitor, an immunosuppressant, an anti-metabolite, a COX-2 inhibitor, a nucleoside (purine or pyrimidine) analog, a Ras inhibitor, a farnesyl transferase inhibitor, or a histone deacetylase inhibitor.

SUMMARY OF THE INVENTION

In one embodiment, the present invention includes a composition for treating a cancer comprising: an antineoplastic drug; and an inhibitor of chromosome maintenance region 1 (CRM1) protein expression or activity, wherein the inhibitor of CRM1 enhances the anti-neoplastic effect of the antineoplastic drug. In one aspect, the antineoplastic drug is a platinum-based antineoplastic drug selected from at least one of cisplatin, carboplatin, oxaliplatin, satraplatin, picoplatin, nedaplatin, triplatin or lipoplatin. In another aspect, the antineoplastic drug is a taxane, a tyrosine-kinase inhibitor, an inhibitor of epidermal growth factor receptor, or an immunotherapy. In another aspect, the inhibitor of CRM1 is at least one of Leptomycin A, Leptomycin B, Leptomycin analogs, an RNA that interferes with CRM1 expression or mRNA, ratjadone, valtrate, acetoxychavicol acetate, an oral CRM1 inhibitor (CBS9106), a selective inhibitor of nuclear export (SINE), a natural compound that inhibits CRM1, or a natural product such as curcumin. In another aspect, the cancer is defined further as a CRM1 over-expressing cancer. In another aspect, the cancer is defined further as having post-translationally modified p53 that modulates p53 activity. In another aspect, the cancer is defined further as having post-translationally modified p53, therein the modification is a ribosylation or a phosphorylation. In another aspect, the cancer is defined further as having post-translationally modified p53, wherein the modification is a phosphorylation at threonine residue 55, serine residues 9, 15, 20, 46, or 392 of the p53 protein. In another aspect, the amount of the antineoplastic drug is suboptimal for the treatment of the cancer without the inhibitor of CRM1. In another aspect, the cancer is selected from a lung, a pancreatic, a leukemia, a glioma, a cervical, an ovarian, an osteosarcoma, multiple myeloma, or a renal cell cancer. In another aspect, the cancer is a lung cancer, and the lung cancer is selected from non-small cell lung cancer at least one of an adenocarcinoma, a squamous cell carcinoma, or a large cell carcinoma, or a small cell lung cancer.

In another embodiment, the present invention includes a method of treating a cancer comprising: identifying a patient with a cancer; and providing the patient with an effective amount of a combination of an antineoplastic drug and an inhibitor of CRM1, wherein the inhibitor of CRM1 enhances the anti-neoplastic effect of the antineoplastic drug. In one aspect, the step of identifying the patient with lung cancer is defined further as comprising at least one of determining that a sample of lung tissue suspected of being cancerous overexpresses a chromosome maintenance region 1 (CRM1) gene or a change in the post-translational modification of a p53 protein. In another aspect, the antineoplastic drug is a platinum-based antineoplastic drug selected from at least one of cisplatin, carboplatin, oxaliplatin, satraplatin, picoplatin, nedaplatin, triplatin or lipoplatin. In another aspect, the antineoplastic drug is a taxane, a tyrosine-kinase inhibitor, an inhibitor of epidermal growth factor receptor, or an immunotherapy. In another aspect, the inhibitor of CRM1 is at least one of Leptomycin A, Leptomycin B, Leptomycin analogs, an RNA that interferes with CRM1 expression or mRNA, ratjadone, valtrate, acetoxychavicol acetate, an oral CRM1 inhibitor (CBS9106), a selective inhibitor of nuclear export (SINE), a natural compound that inhibits CRM1, or a natural product such as curcumin. In another aspect, the cancer is defined further as a CRM1 over-expressing cancer.

In another aspect, the cancer is defined further as having post-translationally modified p53 that modulates p53 activity. In another aspect, the cancer is defined further as having post-translationally modified p53, therein the modification is a ribosylation or a phosphorylation. In another aspect, the cancer is defined further as having post-translationally modified p53, wherein the modification is a phosphorylation at threonine residue 55, serine residues 9, 15, 20, 46, or 392 of the p53 protein. In another aspect, the amount of the antineoplastic drug is suboptimal for the treatment of the cancer without the inhibitor of CRM1. In another aspect, the cancer is selected from a lung, a pancreatic, a leukemia, a glioma, a cervical, an ovarian, an osteosarcoma, multiple myeloma, or a renal cell cancer. In another aspect, the cancer is a lung cancer, and the lung cancer is selected from non-small cell lung cancer at least one of an adenocarcinoma, a squamous cell carcinoma, or a large cell carcinoma, or a small cell lung cancer.

In one embodiment, the composition for treating a lung cancer comprises: at least one of cisplatin or lipoplatin; and a leptomycin B, wherein the leptomycin B enhances the anti-neoplastic effect of the cisplatin or lipoplatin against lung cancer. In one aspect, the lung cancer is defined further as a chromosome maintenance region 1 (CRM1) expressing lung cancer. In another aspect, the lung cancer is defined further as having a post-translationally modified p53 protein that modulates the activity of the p53. In another aspect, the composition further comprises an shRNA that knocks down CRM1 expression. In another aspect, the amount of the cisplatin or lipoplatin is suboptimal for the treatment of lung cancer without the leptomycin B.

In another embodiment, the present invention includes a method of diagnosing a cancer comprising: obtaining a biopsy from a patient with a cancer; determining that a sample of tissue suspected of being cancerous overexpresses a chromosome maintenance region 1 (CRM1) gene or a post-translational modification of a p53 protein; and providing the patient with an effective amount of a combination of an antineoplastic drug and an inhibitor of CRM1, wherein the inhibitor of CRM1 enhances the anti-neoplastic effect of the antineoplastic drug if the patient has an increase in expression of a chromosome maintenance region 1 (CRM1) gene or a change in the post-translational modification of a p53 protein when compared to non-cancerous tissue. In one aspect, the antineoplastic drug is a platinum-based antineoplastic drug selected from at least one of cisplatin, carboplatin, oxaliplatin, satraplatin, picoplatin, nedaplatin, triplatin or lipoplatin. In another aspect, the antineoplastic drug is a taxane, a tyrosine-kinase inhibitor, an inhibitor of epidermal growth factor receptor, or an immunotherapy. In another aspect, the inhibitor of CRM1 is at least one of Leptomycin A, Leptomycin B, Leptomycin analogs, an RNA that interferes with CRM1 expression or mRNA, ratjadone, valtrate, acetoxychavicol acetate, an oral CRM1 inhibitor (CBS9106), a selective inhibitor of nuclear export (SINE), a natural compound that inhibits CRM1, or curcumin. In another aspect, the cancer is defined further as a CRM1 over-expressing cancer. In another aspect, the cancer is defined further as having post-translationally modified p53 that modulates p53 activity. In another aspect, the cancer is defined further as having post-translationally modified p53, therein the modification is a ribosylation or a phosphorylation. In another aspect, the cancer is defined further as having post-translationally modified p53, wherein the modification is a phosphorylation at threonine residue 55, serine residues 9, 15, 20, 46, or 392 of the p53 protein. In another aspect, the amount of the antineoplastic drug is suboptimal for the treatment of the cancer without the inhibitor of CRM1. In another aspect, the cancer is selected from a lung, a pancreatic, a leukemia, a glioma, a cervical, an ovarian, an osteosarcoma, multiple myeloma, or a renal cell cancer. In another aspect, the cancer is a lung cancer, and the lung cancer is selected from non-small cell lung cancer at least one of an adenocarcinoma, a squamous cell carcinoma, or a large cell carcinoma, or a small cell lung cancer.

BRIEF DESCRIPTION OF THE DRAWINGS

For a more complete understanding of the features and advantages of the present invention, reference is now made to the detailed description of the invention along with the accompanying figures and in which:

FIG. 1A shows IHC staining of CRM1 in lung adenocarcinoma and matched adjacent histologically normal lung tissues from a lung cancer patient (40×). FIG. 1B shows quantitative H score of CRM1 expression in lung tumors and matched adjacent normal lung tissues (n=10). *$P<0.01$ compared to adjacent normal. FIG. 1C shows Quantitative measurement of CRM1 expression in lung tumors and matched adjacent normal lung tissues from tissue microarray (n=59). *$P<0.01$ compared to adjacent normal. FIG. 1D shows hematoxylin and eosin staining (40×) of a case of lung adenocarcinoma from NNK-treated mice. FIG. 1E shows CRM1 protein expression of four representative cases of lung adenocarcinoma from NNK-treated mice (n=8) and four representative normal lung tissues from vehicle-treated controls (n=8) from the same Western blot. The blot was probed for α-tubulin to confirm equal protein loading. *$P<0.01$ compared to the control.

FIG. 2A shows a soft agar colony assay of BEAS-2B cells and NNK-transformed BEAS-2B cells (BEAS-2B$_{NNK}$) (40×). FIG. 2B shows CRM1 and phospho-p53 (Thr55) protein expression in BEAS-2B cells and BEAS-2B$_{NNK}$ cells. *$P<0.05$ compared to BEAS-2B. FIG. 2C shows phospho-p53 (Thr55) protein expression of four representative cases of lung adenocarcinoma from NNK-treated mice (n=8) and four representative normal lung tissues from vehicle-treated controls (n=8) from the same Western blot. The blot was probed for α-tubulin to confirm equal protein loading. *$P<0.01$ compared to the control. FIG. 2D shows phospho-p53 (Thr55) expression in BEAS-2B cells exposed to NNK or vehicle control for 24 and 72 h. Data were obtained from representative samples loaded on the same Western blot for each of 24 and 72 h. Blots were probed for α-tubulin to confirm equal protein loading. *$P<0.05$ compared to the control.

FIGS. 3A to 3C show CRM1 protein expression (a), cell morphology (b, 100×), and soft agar colony assay (c, 40×) in BEAS-2B and BEAS-2B$_{CRM1+}$ cells. The blot was probed for α-tubulin to confirm equal protein loading. *$P<0.01$ compared to BEAS-2B. FIGS. 3D to 3F show CRM1 protein expression after CRM1-siRNA (d) and CRM1-shRNA (e) transfection and soft agar colony assay (f, 40×) in A549 and A549$_{CRM1-}$ cells. Blots were probed for α-tubulin to confirm equal protein loading. *$P<0.05$ compared to A549. FIG. 3G shows tumor growths in xenograft nude mice (strain code 088) implanted with A549 or A549$_{CRM1-}$ cells.

FIG. 4A shows the cytotoxic effects of Cis on A549 or A549$_{CRM1-}$ cells at 24-72 h. Data are expressed as the percentage by comparing to vehicle control. Values are represented as means±SD, n=6. Experiments performed in triplicate yielded similar results. FIG. 4B shows the cytotoxic effects of Cis and/or LMB on A549 cells at 24-72 h. Data are expressed as the percentage by comparing to vehicle control for Cis and LMB for Cis+LMB. Values are represented as means±SD, n=6. Experiments performed in triplicate yielded similar results. FIG. 4C shows the distribution of cell population in different cell cycle phases in A549 after Cis and/or LMB treatment. Experiments were performed in triplicate and yielded similar results. Cis25: 25 μM cisplatin, LMB0.5: 0.5 nM LMB, and Cis25+LMB0.5: 25 μM cisplatin+0.5 nM LMB.

FIG. 5A shows a representative PCR array gene table and RT-PCR gene arrays in A549 cells treated with Cis or Cis+LMB. The heat map demonstrating fold regulation expression data. Gray: genes were not measurable. Cis25: 25 μM cisplatin, and Cis25+LMB0.5: 25 μM cisplatin+0.5 nM LMB. FIG. 5B shows a Western blot analyses of PARP1, p21, and survivin protein expression in A549 cells after Cis and/or LMB treatment. Blots were probed for α-tubulin to confirm equal protein loading.

DETAILED DESCRIPTION OF THE INVENTION

Figure 1A:
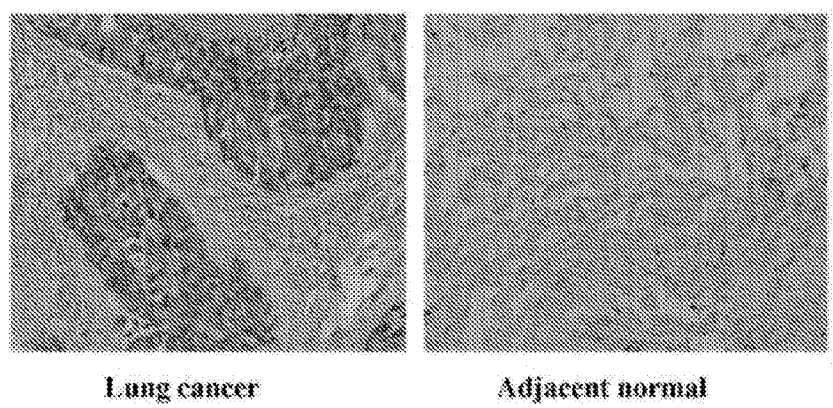
FIGS. 1A-1E CRM1 show expression in lung tumors from human lung cancer patients and NNK-induced lung adenocarcinoma in mice.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "antineoplastic drug" refers to a compound or compounds that slow or inhibit the division of cancerous cells or that kill the cancerous cells. Non-limiting examples of anti-neoplastic drugs include platinum-based antineoplastic drug selected from at least one of cisplatin, carboplatin, oxaliplatin, satraplatin, picoplatin, nedaplatin, triplatin, lipoplatin, taxane, a tyrosine-kinase inhibitor, an inhibitor of epidermal growth factor receptor, or an immunotherapy. In one example, the amount of the antineoplastic drug is provided at a suboptimal for the treatment of the cancer without the inhibitor of CRM1.

As used herein, the term "inhibitor of chromosome maintenance region 1 (CRM1) protein expression or activity" refers to a compound or compounds that either inhibit the transcription of CRM1 mRNA, that inhibit or sequester the mRNA, the inhibit the production of CRM1 mRNA into protein, or that inhibit specifically or non-specifically the activity of CRM1 protein. Non-limiting examples of CRM1 inhibitors include Leptomycin A, Leptomycin B, Leptomycin analogs, an RNA that interferes with CRM1 expression or mRNA, ratjadone, valtrate, acetoxychavicol acetate, an oral CRM1 inhibitor (CBS9106), a selective inhibitor of nuclear export (SINE), a natural compound that inhibits CRM1, or natural products such as curcumin. Human CRM1 has an amino acid sequence of UniProt Number O14980, and mRNA sequence of NCBI Reference Sequence NM_003400.3, both incorporated herein by reference.

As used herein, the cancers that are defined by overexpression of CRM1, or an increase in CRM1 activity, include, e.g., cancers in which there is an over-expression of CRM1, the CRM1 has an increased activity, or have a post-translationally modified p53 protein that has a modified activity, e.g., post-translationally modified p53, therein the modification is a ribosylation or a phosphorylation such as phosphorylation at threonine residue 55, serine residues 9, 15, 20, 46, or 392 of the p53 protein. Examples of cancers that are defined by overexpression of CRM1 can include lung, pancreatic, leukemia, glioma, cervical, ovarian, osteosarcoma, multiple myeloma, or renal cell cancer. Examples of lung cancer include non-small cell lung cancer at least one of an adenocarcinoma, a squamous cell carcinoma, or a large cell carcinoma, or a small cell lung cancer.

Lung cancer remains the leading cause of cancer deaths worldwide and in the United States. Due to the prevalence of tumor chemo-resistance, the clinical response of lung cancer to chemotherapy is poor. Combinative chemotherapy could be an effective and clinically practical strategy for interfering with these processes. The inventors demonstrate that a combination therapy using initial doxorubicin treatment and subsequent blocking of the chromosome maintenance region 1 (CRM1, also known as exportin 1) protein by antibiotic Leptomycin B treatment is an effective therapeutic strategy for lung cancer treatment. Furthermore, the inventors demonstrate that that blocking of CRM1 through leptomycin B (at a very low, non-cytotoxic dosage) or other methods for reducing CRM1 expression leads to lung cancer cell apoptosis. As such the combination taught herein and methods of using the same are potent lung cancer therapeutics, especially when combined with other chemotherapeutic drugs such as Cisplatin or Docetaxel that are commonly used in lung cancer clinics.

In spite of extensive investigations, the molecular mechanisms of lung tumorigenesis are not completely understood and the effective therapy of lung cancer is in great demand Several studies have shown that chromosome maintenance region 1 (CRM1), a nuclear export receptor for various cancer-associated 'cargo' proteins, plays an important role in the development of several human cancers. The present inventors have determined that this protein may also play an important role in lung cancer development. In this study, the inventors investigated CRM1 expression and p53 protein post-translational modification in human lung tumor tissues and lung tissues from a mouse model for lung adenocarcinoma mediated by exposure to the tobacco-carcinogen, 4-(methylnitrosamino)-1-(3-pyridyl)-1-butanone (NNK).

The data shown herein demonstrates that CRM1 was overexpressed in tumor tissues from both lung cancer patients and NNK-treated mice and in NNK-transformed human lung epithelial cells. Furthermore, stably over-expressed CRM1 in human lung epithelial cells either through a plasmid vector led to cellular malignant transformation. Interestingly, changes in CRM1 expression levels in these tissues and cells were associated with the changes in the phosphorylation at threonine residue 55 of the p53 protein. In addition, the potential of targeting CRM1 as an adjuvant therapy in combination with cisplatin was also evaluated. These results are the first to show that CRM1 inhibition using shRNA led to decreased tumorigenicity of lung adenocarcinoma cell A549. Cytotoxic effects of cisplatin were more remarkable on CRM1-shRNA transfected A549 cells and in combination of leptomycin B (LMB, a CRM1 inhibitor) in both in vitro and in vivo models with the involvement of cancer target genes. These data demonstrate that CRM1 plays an important role in lung carcinogenesis and provide a novel target for lung cancer therapy, which is targeted and shown herein to provide a novel therapy for lung cancer.

Lung cancer continues to be the leading cause of cancer deaths in the United States and worldwide[1,2]. Non-small cell lung cancer (NSCLC) remains the predominant form of lung cancer (about 85%)[3,4]. With some improvements in surgical techniques and combined therapies over the last several decades, the relative survival rate for lung cancer has increased slightly. However, lung cancer remains extremely lethal, with a 5-year survival rate of only about 15% in the United States[2]. Unclear molecular mechanisms, lack of early diagnostic biomarkers, and deficiency of targeted therapy in lung cancer are some of the major reasons that its incidence, diagnosis, and prognosis remain relatively unchanged.

Evidence shows that 80-90% of lung cancers are directly or indirectly traceable to tobacco use[5]. More than 60 known carcinogens have been identified in cigarette smoke[8,9], among which N-Nitrosamines play major roles in carcinogenesis. NNK [4-(methylnitrosamino)-1-(3-pyridyl)-1-butanone] is an important nitrosamine with highly carcinogenic activities and a consistent presence in relatively considerable amounts in cigarette smoke[8]. NNK has been shown to have lung-selective toxicity and induce primarily lung adenocarcinoma in a variety of laboratory animals[6,9]. The development of lung cancer has been extensively investigated in the past forty years. Some of these studies, including our previous studies[10-12], have revealed a frequent occurrence of mutations in several proto-oncogenes and tumor suppressor genes, including p53 gene, and such alterations have been associated with the initiation and progression of lung cancer.

In addition to mutations in oncogenes and tumor suppressor genes, accumulated evidence has also shown that stage-specific genes turn on or off during the process of cancer development[13]. For instance, in eukaryotic cells nuclear-cytoplasmic transport is critical for normal biological functions, such as transcription and cell cycle regulation[14,15]. CRM1, the best characterized nuclear export receptor, was first identified in the yeast *Schizosaccharomyces prombe* (*S. pombe*)[16] and has been found as a conserved gene in eukaryotes. CRM1 protein, facilitated by Ran, plays an essential role in nuclear export signal (NES)-dependent nuclear export of various cancer-associated 'cargo' proteins[17-20], including both tumor suppressors and pro-oncogenes, which control genomic stability, cell cycle arrest, and apoptosis, such as p53, epidermal growth factor receptor (EGFR), protein kinase 1 (Akt1), survivin, and so on. The structure of CRM1 protein contains a highly conserved central region involved in RanGTP-dependent NES recognition and cysteine residue covalently modified by leptomycin B (LMB)[21]. LMB, an antifungal agent, is a highly specific and potent inhibitor of CRM1 function by irreversibly reacting with a Cys residue (Cys528 in humans) near or within the cargo binding domain of CRM1[22]. Elevated CRM1 protein expression has been identified in various human tumors[23-27], but no study has been conducted on lung cancer.

The inventors have shown that decreased CRM1 plays an important role in the initial response of lung epithelial cell to tobacco carcinogen and the tumor formation of a bi-transgenic lung tumor model[28,29]. In order to get further insight into the mechanisms by which CRM1 is involved in late phase of lung cancer development, the inventors have analyzed CRM1 expression in lung tumor tissues from lung cancer patients, lung cancer cells, and NNK-treated mice and human lung epithelial cells. In addition, the therapeutic potential of targeting CRM1 in lung cancer was also investigated.

Tissue specimens and tissue microarray (TMA). Lung cancer tissues consisted of paraffin-embedded lung tumors and included 5 adenocarcinomas and 5 squamous cell carcinomas. All samples were collected under protocols approved by the local Institutional Review Board (IRB). These patients were all smokers and consisted of 9 males and 1 female, with an age range of 26-78 years. All slides were stained with hematoxylin and eosin and reviewed by a pathologist to confirm the histological presence of tumor. This set of samples was used as a training set to evaluate CRM1 expression in lung cancer tissues as compared to matched adjacent histologically normal tissues.

Tissue microarray was purchased from IMGENEX and was made from 59 lung cancer tissues (IMH-305) or their matching normal adjacent tissues (IMH-340). These specimens were obtained from 47 males and 12 females with an average age of 60.8 years (range 33-81). They included 15 adenocarcinomas (7 stage I, 4 stage II, and 4 stage III), 37 squamous cell carcinomas (12 stage I, 19 stage II, and 6 stage III), 5 large cell carcinomas (4 stage I and 1 stage II), and 2 carcinosarcomas (1 stage I and 1 stage II). This set of samples was used as a testing set to validate the finding of CRM1 expression.

Immunohistochemistry (IHC) and immunocytochemistry (ICC). The signals of CRM1 or p53 were evaluated by IHC or ICC using VECTASTAIN ABC Kit with DAB as the substrate (Vector Laboratories) following the manufacturer's protocol with modification as described in our previous publications[28,29]. To evaluate CRM1 expression in samples from the training set, stained lung tissue sections were semi-quantified using the "H score" as described in our previous study[28]. Different from the qualitative analysis for the training set, a quantitative measurement of the CRM1 staining (range 0-3: "zero" designates no stain, and "three" defines the darkest stain) was performed for the testing set of samples from TMA. The slides were blindly examined by two individuals.

Human normal lung epithelial cells BEAS-2B with NNK exposure/transformation or CRM1 stable overexpression. Human normal bronchial epithelial cell line BEAS-2B was obtained from American Type Culture Collection (ATCC). (1) For short-term NNK exposure, BEAS-2B cells were treated with 0, 10, 75, or 150 μM NNK for 24 and 72 h in triplicate as described in our previous study[29]; (2) BEAS-$2B_{NNK}$, an in vitro transformed cell model derived from BEAS-2B, was generated by exposure to NNK (15 μM) for 24 h and then continuously sub-cultured for 9 passages. This transformed cell has been shown to be suitable for studying lung carcinogenesis[30]; and (3) BEAS-2B with stably overexpressed CRM1, named BEAS-2B$_{CRM1+}$, was generated by CRM1 expression plasmid construct transfection (RC206004, OriGene) and G418 (Invitrogen) selection in BEAS-2B cells. Similarly, BEAS-2B was transfected with vector control for comparison. BEAS-2B, BEAS-2B$_{NNK}$, and BEAS-2B$_{CRM1+}$ cells were cultured in LHC-9 medium (Invitrogen) containing 100 U penicillin/mL and 100 µg/mL streptomycin.

CRM1 stable knockdown in A549 cells (A549$_{CRM1-}$). To further study the significance of CRM1 in lung carcinogenesis, the inventors designed CRM1-siRNA oligonucleotides and their efficacy for knocking down CRM1 was compared to that of commercially available CRM1-siRNA from Santa Cruz (Santa Cruz, Calif.). A short hairpin siRNA (shRNA) was designed using one specific effective siRNA for stable transfection. After transformation, selection, propagation, purification, and sequencing, the purified pSilencer 4.1-CMV plasmid was transfected into A549 cells. The stable transfected cells were selected by the culture medium containing 1 mg/mL G418 (Invitrogen). Similar approach was used for the control with a scrambled shRNA.

Soft agar colony assay (Anchorage independent growth assay). Cells were suspended at 5×10⁴ cells/mL for BEAS-2B, BEAS-2B$_{NNK}$, and BEAS-2B$_{CRM1+}$ or 2×10⁴ cells/mL for A549 and A549$_{CRM1-}$ cells in growth medium containing 0.35% agar. Cell suspension was added to a 6-well tissue culture plate pre-coated with 0.7% solid agar. After 9-11 days of incubation (9 days for A549 and 11 days for BEAS-2B), the number of colonies/microscope area (6 randomly selected areas/well) was counted and their sizes were analyzed using cell staining (0.005% Crystal Violet) by microscope. This study was done in triplicate.

Mouse model and NNK-induced lung tumors. Male FVB/N mice are an intermediately susceptible strain with regard to spontaneous lung tumor formation and have been used for studies of NNK-induced lung tumorigenesis[31]. Mice were each given two intra-peritoneal injections of 3 mg NNK per week (NNK-treated group, n=8) or 0.9% saline (vehicle control group, n=8). From each group, mice were sacrificed at 32-weeks after the last NNK- or saline-treatment. Lung tissues were fresh frozen or formalin-fixed and paraffin-embedded.

Isolation of total RNA and quantitative real-time PCR (qRT-PCR). Total RNA was isolated using an RiNeasy® plus mini kit (Qiagen) following the manufacturer protocol. One-Step RT-PCR kit with SYBR green was used for amplification of total RNA (75 ng) by following the manufacturer's protocol (BioRad) and our recent publication[32]. The primers sequences used for GAPDH (116 bp) and CRM1 (198 bp) are 5'-GGTGGTCTCCTCTGACT-TCAACA-3' (Forward) (SEQ ID NO:1) and 5'-GTTGCT-GTAGCCAAATTCGTTGT-3' (Reverse) (SEQ ID NO:2), and 5'-GGAACCAGTGCGAAGGAATA-3' (Forward) (SEQ ID NO:3) and 5'-TTTCGCTGGTCCTACTTGCT-3' (Reverse) (SEQ ID NO:4), respectively. Threshold cycle number (Ct value) was analyzed using CFX Manager Software (Bio-Rad). The Ct value of CRM1 was normalized to the Ct value of GAPDH from same sample and the fold change in the expression was calculated by using the ΔΔCt method. Amplification reaction for each sample was performed in triplicates. Non-template control was also included in each study.

Array-based SYBR® Green RT-PCR. Constitutive gene expression profiling was performed using the RT² Profiler™ PCR array to analyze the expression of 84 genes involving in cancer signal pathways (Human Cancer Drug Targets, Qiagen) based on manufacturer's instructions and our previous publications[33, 34]. Studies were performed in duplicate for each group.

p53 mutation analyses. Polymerase chain reaction-single strand conformation polymorphism (PCR-SSCP) analysis and sequencing were performed to detect p53 mutations in exons 5 to 8 using the reagents, primers and conditions previously described.

Cell viability assay. Cell viability was evaluated using the MTT (3-(4,5-dimethylthiazol-2-yl)-2,5-diphenyltetrazolium bromide) assay as previously described[29, 33]. Based on the cytotoxicity of LMB observed in our previous reports[33, 34], 0.5 nM LMB was selected for co-treatment. Studies were performed independently in triplicate.

Analysis of cell cycle by flow cytometry. The cells were harvested after 24 and 48 h of treatment. Based on the cell viability assay, a total of 4 groups of A549 cells with different treatment types were analyzed, including control, 25 µM cisplatin (Cis25), 0.5 nM LMB (LMB0.5), and 25 µM cisplatin+0.5 nM LMB (Cis25+LMB0.5). Cell cycle analysis was conducted by a Guava EasyCyte™ Flow Cytometer (Millipore) as previously described[32, 33]. Each sample was run in triplicate and each experiment was repeated three times.

Western blot analyses. Protein expression levels in A549 cells after cisplatin treatment (0, 10, and 25 µM) with or without LMB (0.5 nM) were evaluated by Western blots as previously described[29, 32, 33]. Immunoblotting was performed using different primary antibodies and α-tubulin as the internal control.

Xenograft animal model. The handling of animals was in accordance with the Institutional Animal Care and Use Committee. Female athymic mice, 7-8 weeks of age and 23.5 g in weight (Charles River Laboratory) received subcutaneous injection of 1×10⁶ A549 or A549$_{CRM1-}$ cells in the lower flank (n=8/group). Tumor volume was measured by a digital caliper (Thermo Fisher Scientific). The major longitudinal diameter (length) and the major transverse diameter (width) were determined. Tumor volume was calculated based on caliper measurements by the following formula: Tumor volume=½ (length×width²).

Treatment of mouse xenografts. Thirty-two female athymic mice, 7-8 weeks of age and 23.5 g in weight (strain code 088, Charles River Laboratory) were each injected subcutaneously with 1×10⁶ lung cancer A549 cells in the lower flank. The mice bearing lung cancer xenografts were divided into 4 study groups and intra-tumorally injected with the following treatments: 1) 0.9% saline (vehicle control, n=8); 2) LMB (2 µg/Kg, n=8); 3) Cis (2.5 mg/Kg, n=8); and 4) Cis (2.5 mg/Kg)+LMB (2 µg/Kg) (Cis+LMB, n=8). All injections were carried out for three times per week. Mice body weights and tumor sizes were measured three times per week.

Statistical analyses. Paired t test, Student t test, one-way analysis of variance (ANOVA) and post hoc tests, factorial ANOVA, and χ2 test were used to compare the difference between groups where appropriate. All analyses were performed using the STATA 9.0 software. Differences with P<0.05 were considered statistically significant.

CRM1 expression in lung tumors from lung cancer patients and from mice treated with NNK.

Figure 1B:
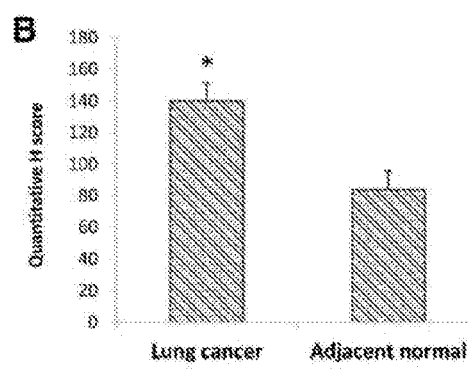
Figure 1C:
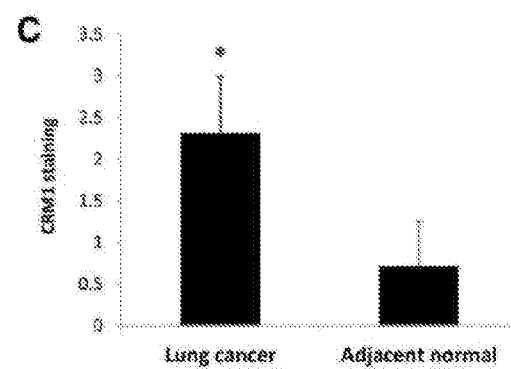

IHC of CRM1 was first performed on a training set of 10 lung tumor tissues from smokers and 10 matched tumor-adjacent histologically normal lung tissues (FIG. 1A). CRM1 expression level was significantly higher in lung tumor tissues (H score: 139.9±11.7), compared with matched normal tissues (H score: 83.9±11.8) (FIG. 1B, P=0.006, paired t test). To validate this result further, CRM1 expression was performed using tissue microarray on a testing set of 59 lung tumor tissues and their matched adjacent histologically normal tissues. CRM1 expression level was significantly higher in tumor tissues, compared with the matched normal tissues (2.3±0.7 in cancer vs. 0.7±0.5 in normal, P<0.001, paired t test, FIG. 1C). Therefore, CRM1 is overexpressed in lung tumor tissues of NSCLC, the major histologic type of lung cancer from smokers.

Figure 1D:
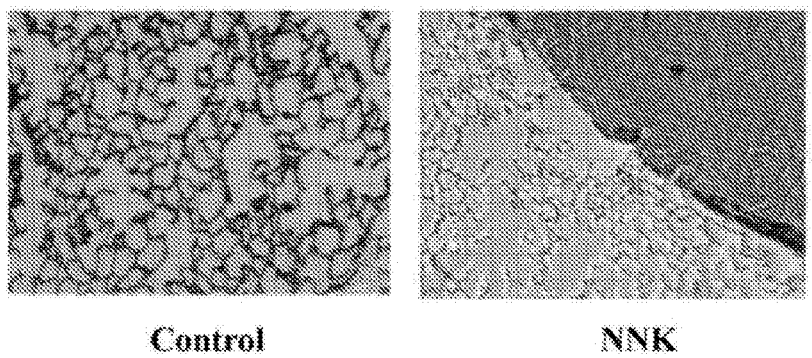
Figure 1E:
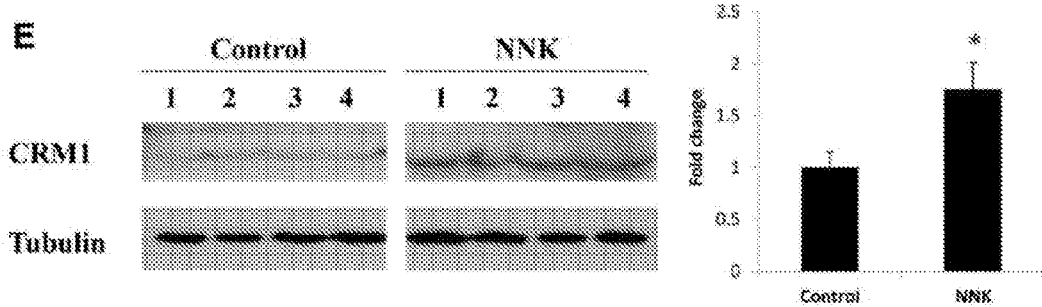
Figure 2A:
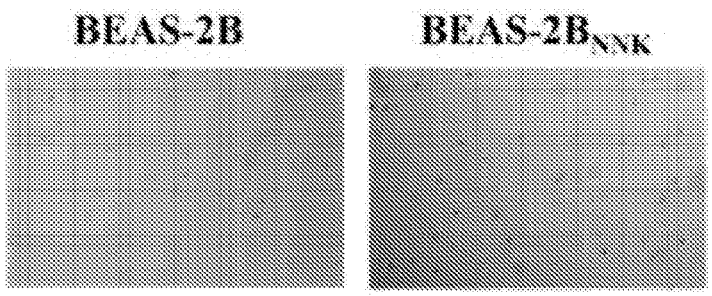
FIGS. 2A-2D show soft agar colony assay and CRM1 and phospho-p53 expressions in BEAS-2B cells after NNK exposure.
Figure 2B:
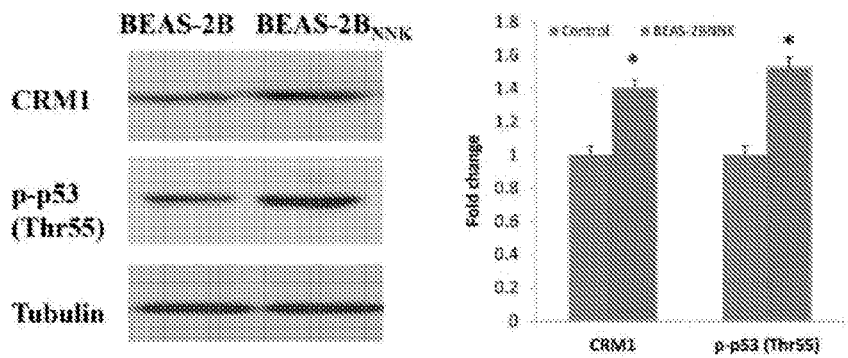

For comparison, lung adenocarcinoma is the only lung tumor subtype found in FBV/N mice treated with NNK (FIG. 1D). Western blot analysis was performed for 8 of such lung tumors and lung tissues from the control. The data showed an increased CRM1 expression in the tumor tissues compared with the normal tissues (FIG. 1E, P<0.01). In order to investigate the effects of a lung carcinogen on the expression of CRM1 in vitro, BEAS-2B cells were transformed with NNK (BEAS-$2B_{NNK}$). Soft agar colony assay showed a significant increase in both colony number and colony size in BEAS-$2B_{NNK}$ as compared with vehicle-treated BEAS-2B cells (FIG. 2A, P<0.05). Furthermore, the transformed cells showed a significant increased CRM1 expression both at the mRNA (2.6 folds) and protein (approximate 1.5 folds) levels as compared to vehicle-treated BEAS-2B cells (FIG. 2B, P<0.05). Therefore, CRM1 is overexpressed in lung tumors from both lung cancer patients and mice treated with the tobacco smoke carcinogen NNK, as well as NNK-transformed lung epithelial cells.

p53 phosphorylation in lung tumors from NNK-treated mice and in NNK-transformed lung epithelial cells.

Figure 2C:
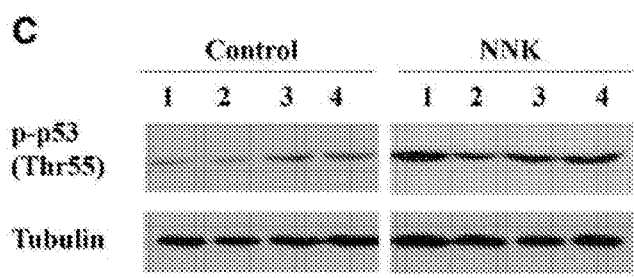
Figure 2C:
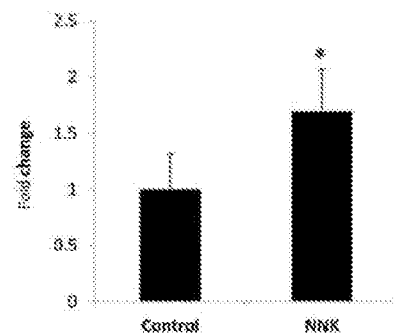
Figure 2D:
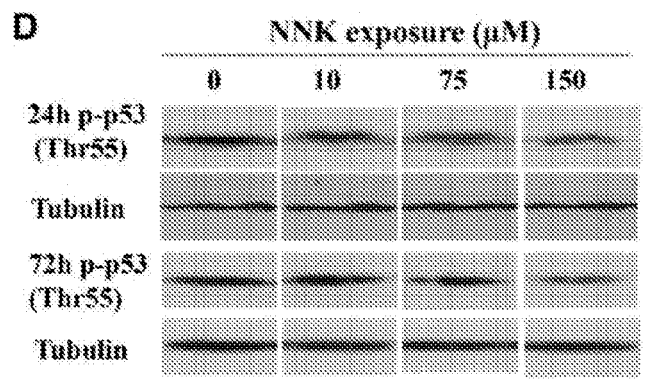
Figure 2D:
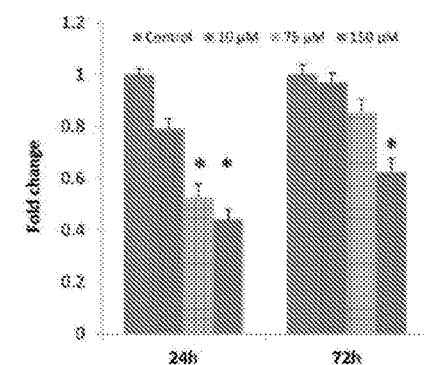

CRM1 plays an important role in the transport of tumor suppressor and oncogene proteins, including p53, from the cell nucleus into the cytoplasm[35, 36]. The inventors' previous study found p53 phosphorylation at Thr55 involved in CRM1-mediated p53 transport to the cytoplasm after treatment of A549 cells with LMB[33]. BEAS-$2B_{NNK}$ cells overexpressed phosphorylated-p53 (p-p53) at Thr55 (FIG. 2B). The inventors determined that p53 mutations were not detected in the lung adenocarcinoma from NNK-treated mice used in this study as the occurrence of such mutations would lead to an accumulation of nonfunctional mutant p53 in these tissues (data not shown). Western blot analysis showed a significant increase in p-p53 at Thr55 in lung tumors from NNK-treated mice from the same tumors analyzed above for CRM1, compared with the normal lung tissues (FIG. 2C, P<0.01). The inventors have previously shown that CRM1 protein expression was decreased, and p53 post-translational modifications were also changed (but the specific residues were not characterized) in BEAS-2B cells at an early exposure to NNK (at 10, 75 and 150 µM) for 24 and 72 h[29]. Protein expression levels of p-p53 at Thr55 in these exposed cells were therefore further analyzed and showed a dose-dependent decrease as compared to the matched control BEAS-2B cells treated with the vehicle (P<0.05, FIG. 2D).

Cellular transformation in BEAS-$2B_{CRM1+}$, decreased colony formation in A549$_{CRM1-}$, and delayed tumor growth after A549$_{CRM1-}$ implantation in the xenograft nude mouse model.

Figure 3A:
FIGS. 3A to 3G show the CRM1 protein expression and soft agar colony assay in BEAS-2B, BEAS-2B$_{CRM1+}$, A549, and A549$_{CRM1-}$ cells, and tumor growths in xenograft nude mice implanted with A549 or A549$_{CRM1-}$ cells.
Figure 3B:
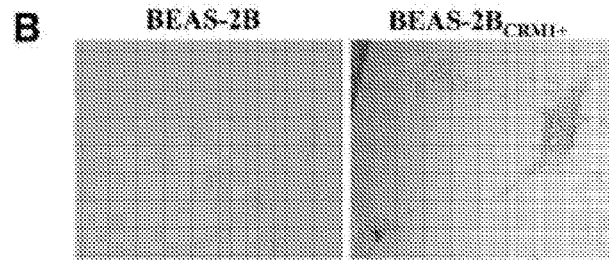
Figure 3C:
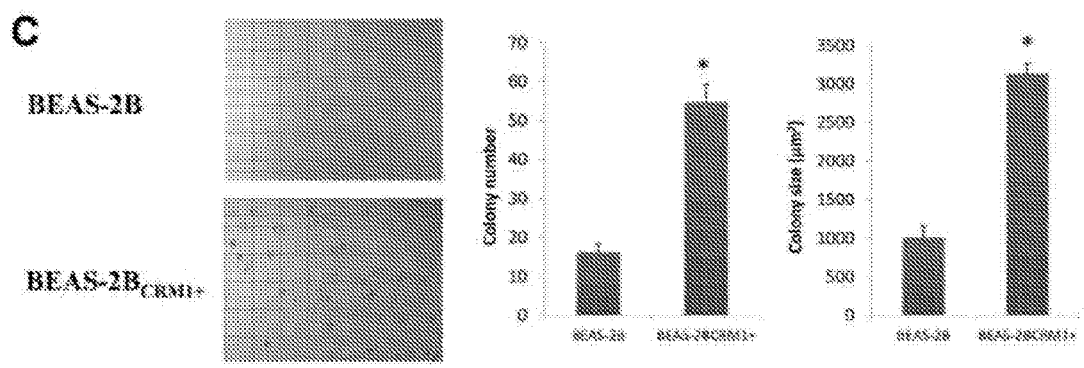

Over a 6-fold increase of CRM1 expression level was observed in BEAS-$2B_{CRM1+}$ cells as compared to either group of control BEAS-2B cells (FIG. 3A). ICC analyses showed that CRM1 expression was remarkably higher and p53 nuclear staining was significantly decreased in BEAS-$2B_{CRM1+}$ compared to BEAS-2B cells (data not shown). BEAS-$2B_{CRM1+}$ cells were prone to form colonies in a regular culture condition (FIG. 3B). Soft agar colony assay showed an increase in both colony number and size in BEAS-$2B_{CRM1+}$ cells as compared with the control BEAS-2B cell groups (FIG. 3C, number of colonies: 54.7±10.2/area for BEAS-$2B_{CRM1+}$ and 16.3±5.6/area for BEAS-2B, P<0.01; size/colony ($\mu m^2$): 3136.1±306.7 for BEAS-$2B_{CRM1+}$ and 1010.5±437.6 for BEAS-2B, P<0.01). These results demonstrate that CRM1 by itself plays a critical role in the in vitro cellular malignant transformation of lung epithelial cells.

Figure 3D:
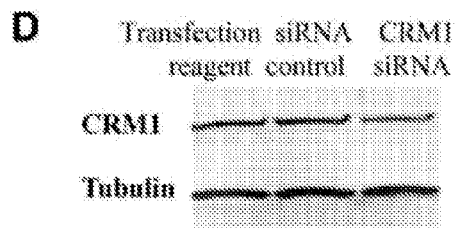
Figure 3E:
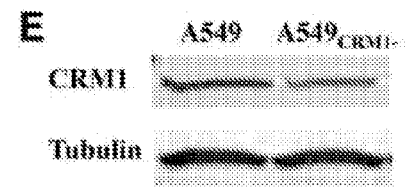
Figure 3F:
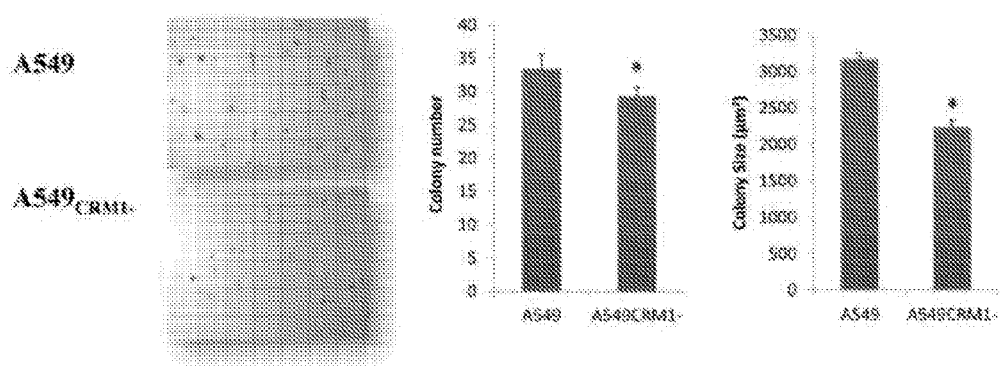
Figure 3G:
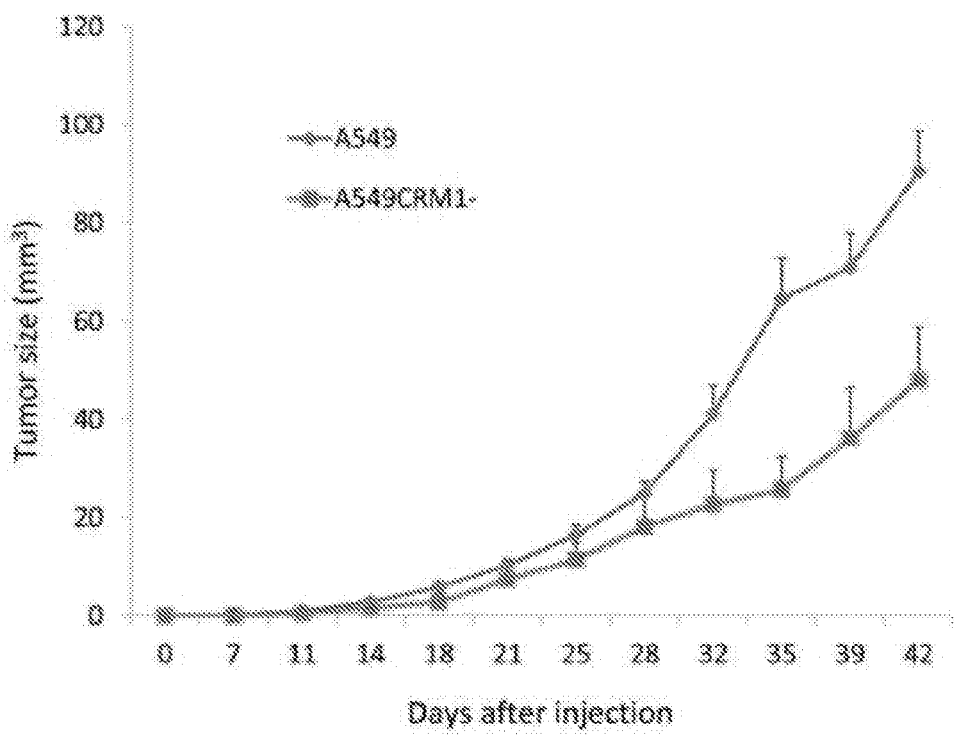

The inventors designed a CRM1-siRNA could significantly knockdown CRM1 in A549 (FIG. 3D), and the efficiency of this single target-specific siRNA is similar and even better to that of commercial CRM1-siRNA products consisting of pools of three to five target-specific siRNAs (data not shown). Knockdown of CRM1 expression in A549$_{CRM1-}$ was confirmed by qRT-PCR (>40% decreases) and Western blot (FIG. 3E). Soft agar assay revealed a decrease in both number and size of colonies in A549$_{CRM1-}$ cells as compared to A549 cells (FIG. 3F, number of colonies: 29.3±3.7/area for A549$_{CRM1-}$ and 33.4±5.7/area for A549, P<0.05; size/colony ($\mu m^2$): 2236.1±273.5 for A549$_{CRM1-}$ and 3169.3±235.8 for A549, P<0.01). No differences in the CRM1 expression level and colony formation were observed between A549 cells without vector transfection and A549 cells transfected with scramble vector (data not shown). FIG. 3G displays the tumor growth curve for the nude mice (strain code 088) implanted with A549$_{CRM1-}$ or A549 cells. Although tumor growth was observed in mice injected with either A549$_{CRM1-}$ or A549 cells, significantly delayed tumor growth was observed in mice injected with A549$_{CRM1-}$ as compared to those injected with A549 (P<0.05). No difference of the body weight and behavior was observed in the mice implanted with A549$_{CRM1-}$ or A549 (data not shown). These data were further confirmed in another xenograft nude mouse model (strain code 490, data not shown).

Effects of Cis and/or LMB on cytotoxicity and cell cycle.

Figure 4A:
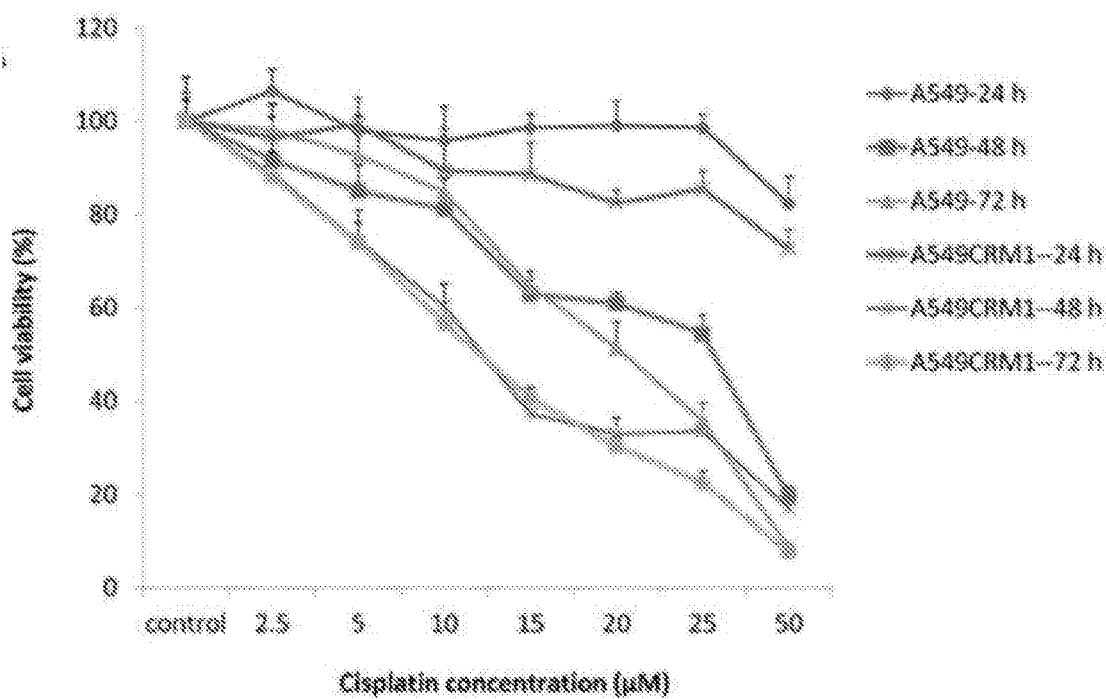
FIGS. 4A to 4C show the effects of Cis and/or LMB on cytotoxicity and cell cycle distribution.
Figure 4B:
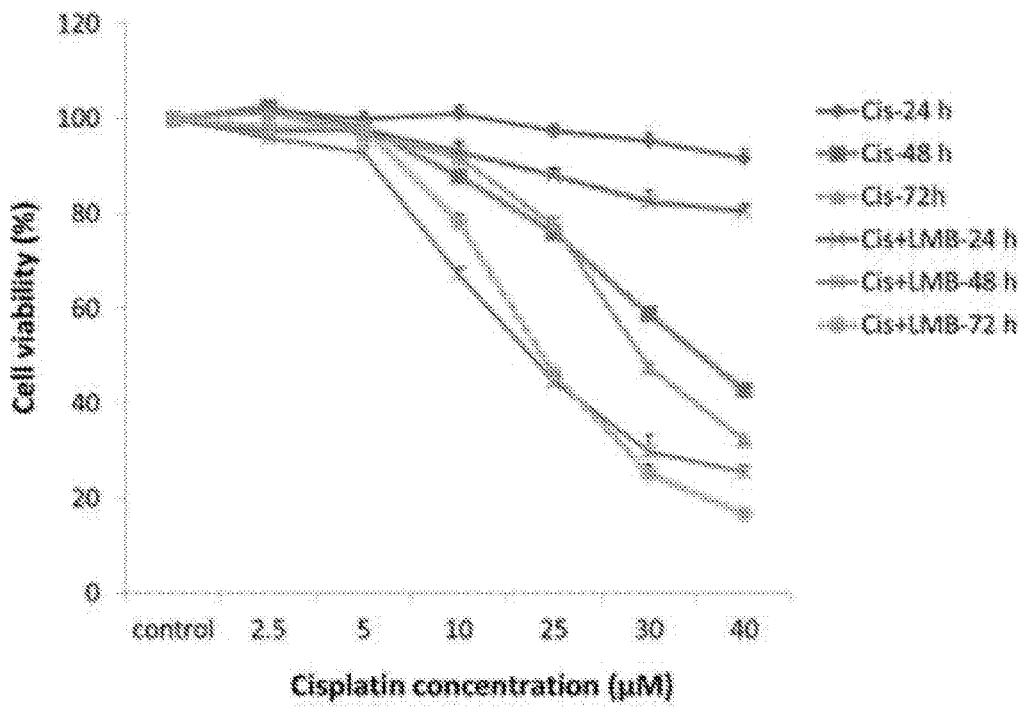
Figure 4C:
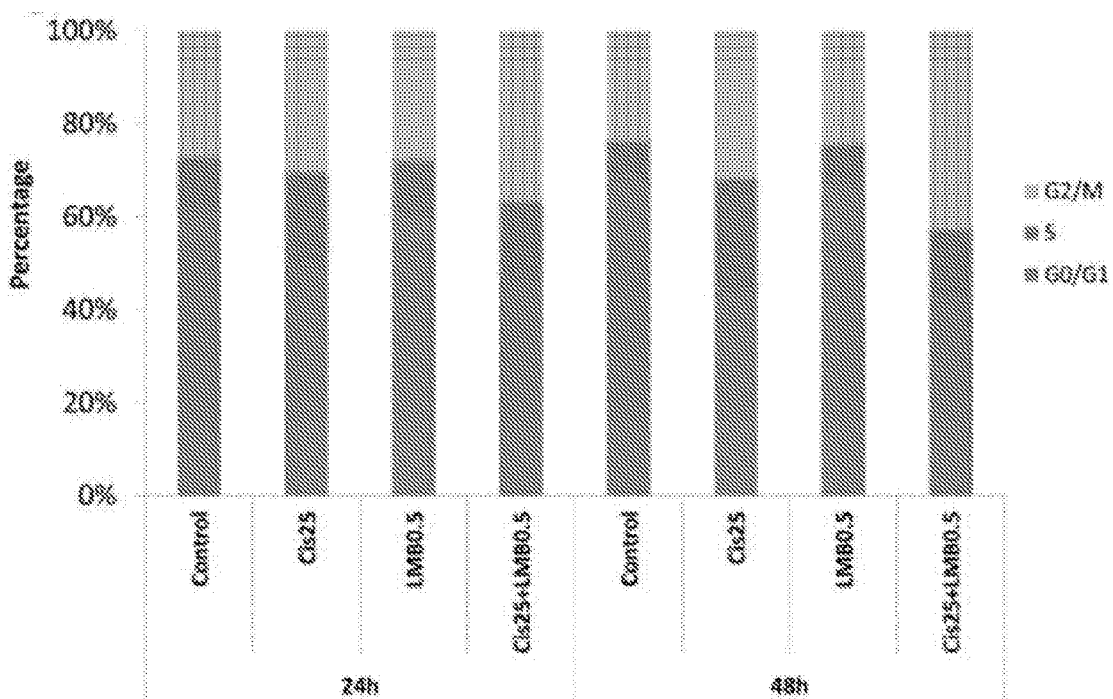

The cytotoxic effects of Cis alone or Cis+0.5 nM LMB (a very low non-toxic dose) on A549 and/or A549$_{CRM1-}$ cells were evaluated. Cis alone significantly inhibited the proliferation of both A549 and A549$_{CRM1-}$ in a dose- and time-dependent manner (P<0.001). Furthermore, A549$_{CRM1-}$ cells were even more sensitive to Cis than A549 cells (FIG. 4A, P<0.05). In addition, co-treatment with Cis and LMB significantly increased the cytotoxic effects of Cis on A549 cells (FIG. 4B, P<0.05). These data indicate that inhibition of CRM1 plays an important role in chemo-sensitizing cancer cells, and targeting CRM1 using LMB provides a novel and efficient adjunct therapy for lung cancer treatment. Cell proliferation inhibition could be the consequence of cell cycle arrest. The cell cycle analysis by flow cytometry of the four treated groups of A549 cells showed as expected that LMB0.5 treatment did not alter the cell cycle distribution of A549 cells, compared with the control. However, the Cis25 and Cis25+LMB0.5 treatment groups resulted in a significantly higher proportion of cells in S and G2/M phases at both 24 and 48 h, compared with the control (P<0.05, FIG. 4C). Moreover, the Cis25+LMB0.5 treatment group showed an accumulation of a significantly higher proportion of cells in the G2/M phase, but a significantly lower proportion of cells in the S phase at both 24 and 48 h, compared with Cis25 (P<0.05, FIG. 4C).

Gene expression alterations after Cis and Cis+LMB treatment and Western blot analyses of PARP1, p21, and surviving.

Figures 5A, 5B:
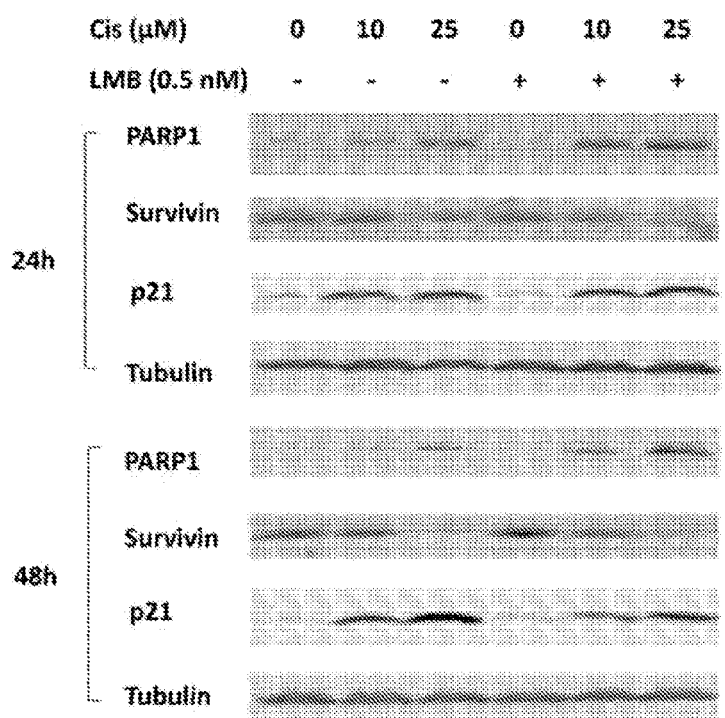
FIGS. 5A and 5B show the effects of Cis and/or LMB on gene/protein expression.

From the 84 genes analyzed (FIG. 5A), there is a significantly decreased expression level of 8 genes (AURKA, AURKB, CDK1, HIF1A, MDM4, PLK1, PLK4, and TNKS) and an increased expression of 4 genes (CTSB, GRB2, MDM2, and NF-κB) in the Cis25 group compared to the control (FIG. 5A, $P<0.05$). Cis25+LMB0.5 treatment significantly increased the expression level of AURKA, HDAC8, PARP2, and TNKS and decreased the expression level of GRB2 and RHOA as compared to the Cis25 group (FIG. 5A, $P<0.05$). No significant difference in the gene expression profile was observed in LMB0.5 group, compared to the control group (data not shown), which is in line with the observation of no differences in cell cycle progression profile between these two treatment groups. qRT-PCR for HIF1A, GRB2, MDM2, and PARP2 were further performed and the results helped confirm the RT-PCR array data (data not shown).

The protein expressions of PARP1, p21, and survivin were then analyzed because of their significant roles in DNA damage, cell cycle, and apoptosis in response to chemotherapeutic agents. Expression levels of PARP1 and p21 were significantly increased in a dose-response manner at both 24 and 48 h after treatment in both the Cis or Cis+LMB treatment groups, compared to those of vehicle-treated cells (FIG. 5B, $P<0.05$). Furthermore, the up-regulation of PARP1 in Cis+LMB was significantly higher, compared with the Cis group (FIG. 5B, $P<0.05$). On the other hand, the survivin expression level was significantly decreased in cells treated with Cis or Cis+LMB, compared to those of controls at both 24 and 48 h after treatment (FIG. 5B, $P<0.05$).

Tumor growth after treatment with Cis and/or LMB in the xenograft nude mouse model.

Figure 6A:
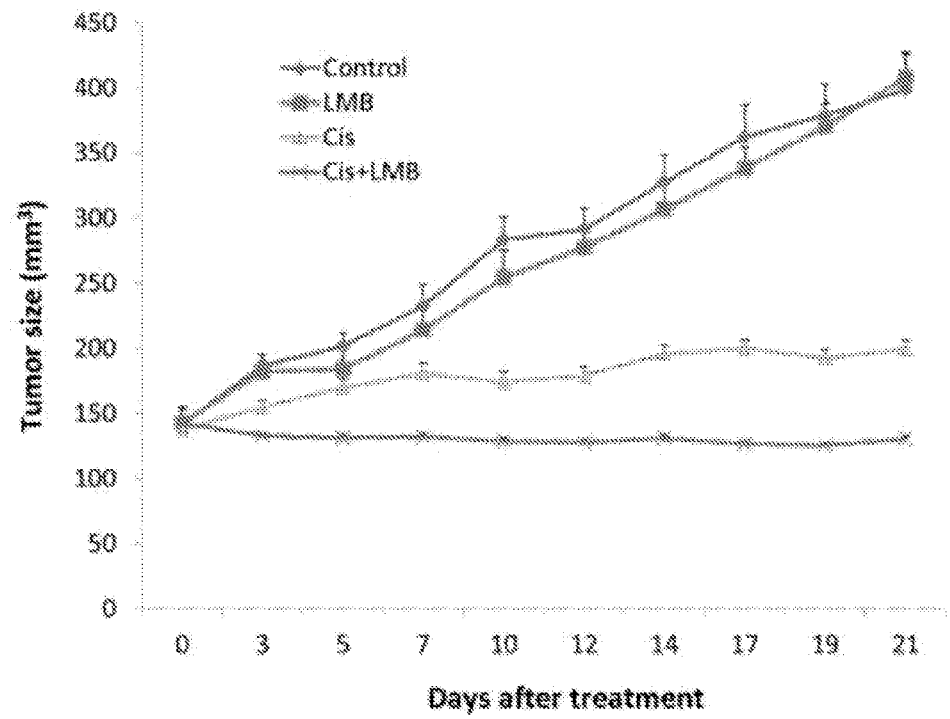
FIGS. 6A and 6B show the effects of Cis and/or LMB on tumor growth (FIG. 6A) and body weight (FIG. 6B) in xenografted nude mice (strain code 088). The Cis treated group showed a significant decrease in tumor growth compared with the vehicle treated group. The Cis+LMB group demonstrated a significant decrease in tumor growth compared with the Cis treated group. Vehicle control: 0.9% saline (n=8), LMB: 2 μg/Kg (n=8), Cis: 2.5 mg/Kg (n=8), and Cis+LMB: Cis (2.5 mg/Kg)+LMB (2 μg/Kg) (n=8).
Figure 6B:
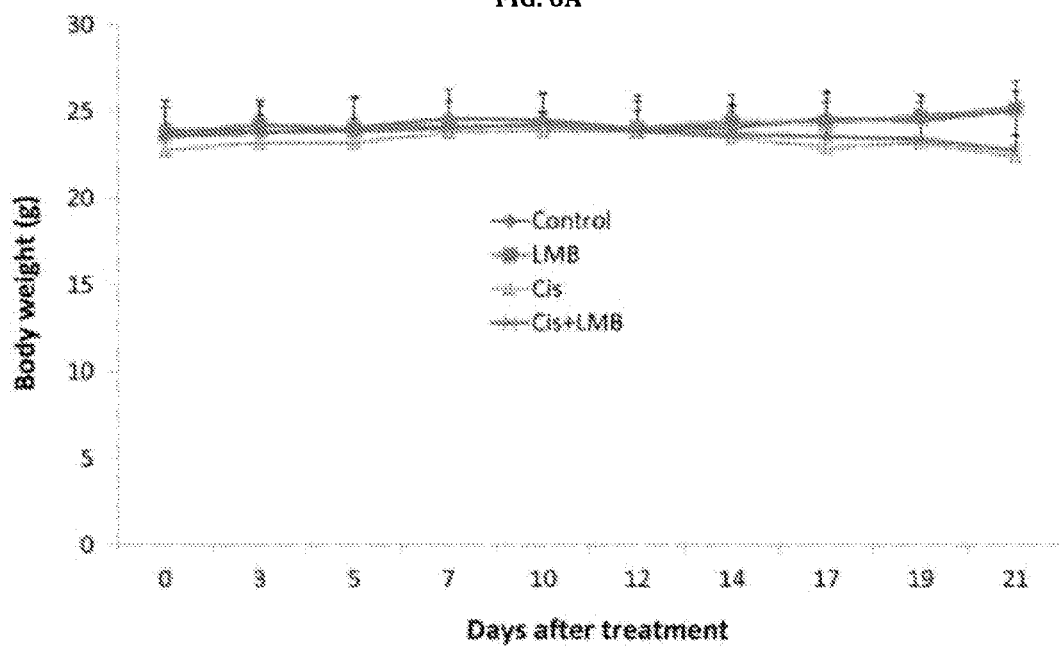

FIG. 6A displays the tumor growth curve for each of the treatment conditions. Tumors injected with Cis significantly delayed tumor growth, compared to the vehicle-treated control ($P<0.01$). Although growth curves followed a similar trend for the tumor treated with either LMB alone or vehicle control, tumors treated with Cis+LMB significantly delayed tumor growth starting at the beginning of the treatment as compared to the Cis group ($P<0.05$). These data demonstrate the synergistic effect of the Cis+LMB co-treatment. Two weeks after treatment with Cis or Cis+LMB, the body weight for mice started to decrease gradually (FIG. 6B) but without deteriorating their behavior and health condition.

In this study, the present inventors demonstrated that CRM1 was frequently overexpressed in NSCLC, particularly adenocarcinoma and squamous cell carcinoma, the two major subtypes of lung tumors from lung cancer patients, suggesting that CRM1 overexpression is involved in lung carcinogenesis. Similar results were observed in lung adenocarcinoma from NNK-treated mice. Furthermore, these data show that CRM1 overexpression in lung epithelial cell line BEAS-2B following NNK exposure or transfection with CRM1 vector resulted in cellular transformation, suggesting that up-regulation of CRM1 is likely one important pathway of cellular malignant transformation. These data also demonstrate a synergistic effect on in vitro cell growth and in vivo tumor growth following CRM1 knockdown/inhibition in combination with standard chemotherapeutics with underlying specific differential gene/protein expression patterns. These results demonstrate a therapeutic intervention by targeting CRM1 for lung cancer treatment.

Increased CRM1 expression has been reported previously in other tumor types, including cervical[26], ovarian[24], and pancreatic[23] cancers, glioma[25], and osteosarcoma[27] and was associated with a negative prognosis. This is the first study showing CRM1 overexpression in lung cancer. It is known that CRM1 is involved in nuclear-cytoplasmic transport of various cancer-associated 'cargo' proteins, such as p53, and other proteins, including p21, p27, EGFR, Akt1, and survivin[17-20]. The observed CRM1 overexpression could in turn lead to dysfunction/inactivation of tumor suppressor proteins or activation of pro-oncogenes by shuttling them out of nucleus to cytoplasm. For instance, besides p53 mutation, another important pathway to p53 regulation/dysregulation is through post-translational modifications, including phosphorylation of wild type p53 and a subsequent alteration in its subcellular localization and function[36, 37]. Phosphorylation at some of such sites is critical for shuttling p53 from the nucleus to cytoplasm to assume its diverse functions. For instance, the phosphorylation at Thr55 is required for MDM2 to promote the CRM1 and p53 interaction and the export of p53 to the cytoplasm, leading to p53 degradation and a decrease in G1 arrest of the cell cycle, while inhibition of Thr55 phosphorylation restored the p53 nuclear localization[35]. The inventors have shown that Thr55 of p53 protein was phosphorylated not only in lung tumors from NNK-treated mice but also in BEAS-2B cells that were transformed following NNK-exposure. Furthermore, these tumors and transformed cells showed CRM1 overexpression, suggesting a mechanism of lung carcinogenesis involving CRM1 overexpression and inactivation of p53 by post-translational phosphorylation of Thr55 in lung carcinogenesis.

Data from in vitro studies using BEAS-2B cells showed a biphasic response of cells to NNK. The initial phase of decrease in CRM1 expression in NNK-exposed cells was observed in our previous study[29]. As shown herein, p-p53 (Thr55) expression was also decreased during this initial phase that may correspond to an adaptive response for cellular repair of NNK-induced DNA damage. Indeed, the inventors have previously observed that following the exposure of BEAS-2B cells with NNK there was an accumulation of p53 in the nucleus and activation of p21 that is important for the process of cell cycle arrest to allow repair of DNA damage[29]. Therefore, decrease in both CRM1 and p-p53 at Thr55 leads to a decrease in export of p53 and a nuclear accumulation of p53 during the early phase of NNK-exposure. Different from this early phase of cellular response to the tobacco carcinogen NNK, in which CRM1 was decreased and concomitantly p53 accumulated in the nucleus probably as a result of an adaptive response to DNA damage repair. It is further demonstrated herein that in the later stage of NNK exposure, there were increased expression levels of CRM1 and p-p53 at Thr55 in both BEAS-$2B_{NNK}$ cells and lung tumors. By way of explanation, and in no way a limitation of the present invention, it has been proposed that a shared complex regulatory loop may exist between CRM1 and p53, and p53 could repress CRM1 promoter activity by interfering with the transcription factor, nuclear factor $Y^{38}$. These results show that NNK-mediated p53 phosphorylation at Thr55 works in parallel with CRM1 expression not only in early phase of NNK exposure but also in NNK-induced cellular transformation. The data from the transfection studies show that exogenous CRM1 modulation by either overexpression in BEAS-2B or knockdown in A549 did not significantly alter expression of p-p53 at Thr55 (data not shown). Therefore, p53 may directly affect CRM1 in NNK-induced carcinogenesis but not vice versa.

Cisplatin is commonly used to treat various types of cancers, including lung cancer. In this study, significant alterations in the expression of genes from protein kinases, cell cycle, transcription factors, and apoptosis were found in A549 cells treated with cisplatin. However, drug resistance in cisplatin-containing regimens is a major issue that prevents better response rates[39]. As cisplatin constitutes a major therapeutic option in clinical settings, the development of chemosensitization strategies for cisplatin has important clinical implications. In the present study, blocking CRM1 expression significantly improves cancer cell sensitization to Cis as revealed by the fact that the drug was more potent in $A549_{CRM1-}$ cells than in A549 cells and that CRM1 inhibition by a co-treatment with Cis+LMB further improved the efficacy of cisplatin in suppressing lung cancer cell proliferation. Thus, combined chemotherapy could be an effective and clinically practical strategy for interfering with chemoresistance. Genes, such as survivin, BAX, BCL2, p53, NF-κB, and ERBB2 are frequently involved in the pathways that sustain cisplatin resistance[39, 40]. In lines with these findings, the inventors show herein an increased expression of NF-κB after treatment with Cisplatin alone while a decreased NF-κB expression in the Cis+LMB treatment. Moreover, p21 and survivin are well known to play a critical role in cell cycle and survival signaling[41, 42]. Accordingly, significant dose-dependent increase in p21 and decrease in survivin expression in cells treated with Cis alone and a more pronounced decrease in survivin in Cis+LMB was observed, compared to Cis treatment alone. In fact, NF-κB is a transcription factor that regulates the expression of numerous genes that are critical for survival, for instance, survivin[43]. NF-κB could be activated by various stimuli such as proinflammatory cytokines, cellular stress, as well as chemotherapeutic agents[43]. Therefore, the inhibition of NF-κB by Cis+LMB leading to a further decrease in survivin compared to Cis alone could be partially responsible for the synergistic effect in A549 lung cancer cells. Finally, the observed changes of other genes such as RHOA, GRB2, and PARP2 in cells treated with Cis+LMB, compared to cells treated with Cis alone, could result in enhancing the sensitization of A549 cells to Cis+LMB treatment on cell proliferation[44-46].

Although the phase I clinical trial of LMB was unsuccessful, the detailed review of this trial only mentions some malaise and anorexia as side effects, which are common for most effective chemotherapeutic drugs[47]. These side effects may diminish if lower doses are administered. In view of the novel CRM1 inhibitors now being developed by different pharmaceutical companies[17, 48-50], the inventors show that the clinical usage of LMB deserves a thorough re-evaluation, especially in combination with other chemotherapeutic drugs at a low and non-toxic dose. The inventors have shown that abrogation of CRM1 through LMB could inhibit lung cancer cell growth and induce cytotoxicity in lung cancer cells, with minimal effects on normal bronchial epithelial cells[34], and the combined therapy using initial doxorubicin treatment and subsequent LMB treatment could improve the effectiveness of therapeutic strategy for lung cancer treatment[33]. The selective and potent anti-tumor cytotoxicity was further confirmed by the silencing of CRM1 using siRNA (data not shown). The in vivo xenograft nude mouse model shown herein is the first demonstration that CRM1 knockdown diminishes the tumorigenicity of lung cancer cells. In addition, the implementation of a very small and non-toxic dose of LMB could boost the efficacy of cisplatin. This combinative chemotherapy showed no-additional side effects. Therefore, adding LMB to the treatment protocol is an effective and clinically practical strategy to not only reduce the drug side effects but also enhance their efficacy, especially in advanced lung cancer, which is characterized by tumor chemo-resistance.

In summary, these results demonstrate that CRM1 overexpression is cooperating with p53 phosphorylation in cellular malignant transformation, a crucial step in lung carcinogenesis. CRM1 inhibition could sensitize the efficacy of cisplatin for lung cancer treatment. As an affirmative, CRM1 is a molecular target in clinical protocols for lung cancer treatment.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Garcia M, Jemal A, Ward E M, et al. *Global Cancer Facts & Figures* 2007. Atlanta, Ga.: American Cancer Society; 2007.
2. Jemal A, Siegel R, Ward E, et al. Cancer statistics, 2009. *CA Cancer J Clin* 2009; 59:225-249.
3. Cancer Facts & Figures. *American Cancer Society* 2014.
4. Devesa S S, Bray F, Vizcaino A P, et al. International lung cancer trends by histologic type: male:female differences diminishing and adenocarcinoma rates rising. *Int J Cancer* 2005; 117:294-299.
5. Freedman N D, Leitzmann M F, Hollenbeck A R, et al. Cigarette smoking and subsequent risk of lung cancer in men and women: analysis of a prospective cohort study. *Lancet Oncology* 2008; 9:649-656.
6. Hecht S S. Carcinogenicity studies of inhaled cigarette smoke in laboratory animals: old and new. *Carcinogenesis* 2005; 26:1488-1492.
7. Wingo P A, Ries L A, Giovino G A, et al. Annual report to the nation on the status of cancer, 1973-1996, with a special section on lung cancer and tobacco smoking. *J Natl Cancer Inst* 1999; 91:675-690.
8. Hecht S S. Cigarette smoking and lung cancer: chemical mechanisms and approaches to prevention. *Lancet Oncology* 2002; 3:461-469.
9. Wogan G N, Hecht S S, Felton J S, et al. Environmental and chemical carcinogenesis. *Seminars in Cancer Biology* 2004; 14:473-486.
10. Gao W M, Mady H H, Melhem M F, et al. Analysis of p53 mutations in histologically normal lung tissues and lung tumors from non-small cell lung cancer patients. *Mol Carcinog* 2009; 48:633-641.
11. Gao W M, Mady H H, Yu G Y, et al. Comparison of p53 mutations between adenocarcinoma and squamous cell carcinoma of the lung: unique spectra involving G to A transitions and G to T transversions in both histologic types. *Lung Cancer* 2003; 40:141-150.
12. Gao W M, Romkes M, Day R D, et al. Association of the DNA repair gene XPD Asp312Asn polymorphism with p53 gene mutations in tobacco-related non-small cell lung cancer. *Carcinogenesis* 2003; 24:1671-1676.
13. Herbst R S, Heymach J V, Lippman S M. Lung cancer. *N Engl J Med* 2008; 359:1367-1380.
14. Cook A, Bono F, Jinek M, et al. Structural biology of nucleocytoplasmic transport. *Annu Rev Biochem* 2007; 76:647-671.
15. Fried H, Kutay U. Nucleocytoplasmic transport: taking an inventory. *Cell Mol Life Sci* 2003; 60:1659-1688.
16. Adachi Y, Yanagida M. Higher order chromosome structure is affected by cold-sensitive mutations in a *Schizosaccharomyces pombe* gene crm1+ which encodes a 115-kD protein preferentially localized in the nucleus and its periphery. *J Cell Biol* 1989; 108:1195-1207.
17. Mutka S C, Yang W Q, Dong S D, et al. Identification of nuclear export inhibitors with potent anticancer activity in vivo. *Cancer Res* 2009; 69:510-517.
18. Xu L, Massague J. Nucleocytoplasmic shuttling of signal transducers. *Nat Rev Mol Cell Biol* 2004; 5:209-219.
19. Kudo N, Khochbin S, Nishi K, et al. Molecular cloning and cell cycle-dependent expression of mammalian CRM1, a protein involved in nuclear export of proteins. *J Biol Chem* 1997; 272:29742-29751.
20. Foo R S, Nam Y J, Ostreicher M J, et al. Regulation of p53 tetramerization and nuclear export by ARC. *Proc Natl Acad Sci USA* 2007; 104:20826-20831.
21. Petosa C, Schoehn G, Askjaer P, et al. Architecture of CRM1/Exportin1 suggests how cooperativity is achieved during formation of a nuclear export complex. *Mol Cell* 2004; 16:761-775.
22. Kudo N, Matsumori N, Taoka H, et al. Leptomycin B inactivates CRM1/exportin 1 by covalent modification at a cysteine residue in the central conserved region. *Proc Natl Acad Sci USA* 1999; 96:9112-9117.
23. Huang W Y, Yue L, Qiu W S, et al. Prognostic value of CRM1 in pancreas cancer. *Clin Invest Med* 2009; 32:E315.
24. Noske A, Weichert W, Niesporek S, et al. Expression of the nuclear export protein chromosomal region maintenance/exportin 1/Xpo1 is a prognostic factor in human ovarian cancer. *Cancer* 2008; 112:1733-1743.
25. Shen A, Wang Y, Zhao Y, et al. Expression of CRM1 in human gliomas and its significance in p27 expression and clinical prognosis. *Neurosurgery* 2009; 65:153-159; discussion 159-160.
26. van der Watt P J, Maske C P, Hendricks D T, et al. The Karyopherin proteins, Crm1 and Karyopherin beta1, are overexpressed in cervical cancer and are critical for cancer cell survival and proliferation. *Int J Cancer* 2008; 124:1829-1840.
27. Yao Y, Dong Y, Lin F, et al. The expression of CRM1 is associated with prognosis in human osteosarcoma. *Oncol Rep* 2009; 21:229-235.
28. Chen L, Moore J E, Samathanam C, et al. CRM1-dependent p53 nuclear accumulation in lung lesions of a bitransgenic mouse lung tumor model. *Oncol Rep* 2011; 26:223-228.
29. Chen L, Shao C, Cobos E, et al. 4-(methylnitrosamino)-1-(3-pyridyl)-1-butanone [corrected] induces CRM1-dependent p53 nuclear accumulation in human bronchial epithelial cells. *Toxicological sciences: an official journal of the Society of Toxicology* 2010; 116:206-215.

30. Langenfeld J, Lonardo F, Kiyokawa H, et al. Inhibited transformation of immortalized human bronchial epithelial cells by retinoic acid is linked to cyclin E down-regulation. *Oncogene* 1996; 13:1983-1990.

31. Stabile L P, Rothstein M E, Keohavong P, et al. Therapeutic targeting of human hepatocyte growth factor with a single neutralizing monoclonal antibody reduces lung tumorigenesis. *Mol Cancer Ther* 2008; 7:1913-1922.

32. Zhu W, Cromie M M, Cai Q, et al. Curcumin and Vitamin E Protect against Adverse Effects of Benzo[a]pyrene in Lung Epithelial Cells. *PloS one* 2014; 9:e92992.

33. Lu C, Shao C, Cobos E, et al. Chemotherapeutic sensitization of leptomycin B resistant lung cancer cells by pretreatment with doxorubicin. *PloS one* 2012; 7:e32895.

34. Shao C, Lu C, Chen L, et al. p53-Dependent anticancer effects of leptomycin B on lung adenocarcinoma. *Cancer chemotherapy and pharmacology* 2011; 67:1369-1380.

35. Cai X, Liu X. Inhibition of Thr-55 phosphorylation restores p53 nuclear localization and sensitizes cancer cells to DNA damage. *Proc Natl Acad Sci USA* 2008; 105:16958-16963.

36. Kanai M, Hanashiro K, Kim S H, et al. Inhibition of Crm1-p53 interaction and nuclear export of p53 by poly(ADP-ribosyl)ation. *Nature Cell Biology* 2007; 9:1175-1183.

37. Jimenez G S, Khan S H, Stommel J M, et al. p53 regulation by post-translational modification and nuclear retention in response to diverse stresses. *Oncogene* 1999; 18:7656-7665.

38. van der Watt P J, Leaner V D. The nuclear exporter, Crm1, is regulated by NFY and Sp1 in cancer cells and repressed by p53 in response to DNA damage. *Biochim Biophys Acta* 2011; 1809:316-326.

39. Galluzzi L, Senovilla L, Vitale I, et al. Molecular mechanisms of cisplatin resistance. *Oncogene* 2012; 31:1869-1883.

40. Oiso S, Ikeda R, Nakamura K, et al. Involvement of NF-kappaB activation in the cisplatin resistance of human epidermoid carcinoma KCP-4 cells. *Oncol Rep* 2012; 28:27-32.

41. el-Deiry W S, Tokino T, Velculescu V E, et al. WAF1, a potential mediator of p53 tumor suppression. *Cell* 1993; 75:817-825.

42. Lin M T, Lee R C, Yang P C, et al. Cyclooxygenase-2 inducing Mcl-1-dependent survival mechanism in human lung adenocarcinoma CL1.0 cells. Involvement of phosphatidylinositol 3-kinase/Akt pathway. *J Biol Chem* 2001; 276:48997-49002.

43. Chen W, Li Z, Bai L, et al. NF-kappaB in lung cancer, a carcinogenesis mediator and a prevention and therapy target. *Frontiers in bioscience* 2011; 16:1172-1185.

44. Etienne-Manneville S, Hall A. Rho GTPases in cell biology. *Nature* 2002; 420:629-635.

45. Kleine H, Herrmann A, Lamark T, et al. Dynamic subcellular localization of the mono-ADP-ribosyltransferase ARTD10 and interaction with the ubiquitin receptor p62. *Cell communication and signaling: CCS* 2012; 10:28.

46. Lin C C, Melo F A, Ghosh R, et al. Inhibition of basal FGF receptor signaling by dimeric Grb2. *Cell* 2012; 149:1514-1524.

47. Newlands E S, Rustin G J, Brampton M H. Phase I trial of elactocin. *Br J Cancer* 1996; 74:648-649.

48. Gademann K. Controlling protein transport by small molecules. *Curr Drug Targets* 2011; 12:1574-1580.

49. Ranganathan P, Yu X, Na C, et al. Preclinical activity of a novel CRM1 inhibitor in acute myeloid leukemia. *Blood* 2012; 120:1765-1773.

50. Sakakibara K, Saito N, Sato T, et al. CBS9106 is a novel reversible oral CRM1 inhibitor with CRM1 degrading activity. Blood 2012; 118:3922-3931.

What is claimed is:

1. A composition for treating a cancer comprising:
an antineoplastic drug, wherein the antineoplastic drug is a platinum-based antineoplastic; and
an inhibitor of chromosome maintenance region 1 (CRM1) protein expression or activity, wherein the inhibitor of CRM1 enhances the anti-neoplastic effect of the antineoplastic drug, wherein the cancer is selected from the group consisting of lung, pancreatic, leukemia, a glioma, cervical, ovarian, an osteosarcoma, multiple myeloma, and a renal cancer.

2. The composition of claim 1, wherein the platinum-based antineoplastic drug selected from at least one of cisplatin, carboplatin, oxaliplatin, satraplatin, picoplatin, nedaplatin, triplatin or lipoplatin.

3. The composition of claim 1, wherein the antineoplastic drug is a taxane or an inhibitor of epidermal growth factor receptor.

4. The composition of claim 1, wherein the inhibitor of CRM1 is at least one of Leptomycin A, Leptomycin B, Leptomycin analogs, an RNA that interferes with CRM1 expression or mRNA, ratjadone, valtrate, acetoxychavicol acetate, an oral CRM1 inhibitor (CBS9106), a selective inhibitor of nuclear export (SINE), a natural compound that inhibits CRM1, or curcumin.

5. The composition of claim 1, wherein the cancer is defined further as a CRM1 over-expressing cancer.

6. The composition of claim 1, wherein the cancer is defined further as having a modified p53 with deregulated p53 activity.

7. The composition of claim 1, wherein the cancer is defined further as having post-translationally modified p53, therein the modification is a ribosylation or a phosphorylation.

8. The composition of claim 1, wherein the cancer is defined further as having post-translationally modified p53, wherein the modification is a phosphorylation at threonine residue 55, serine residues 9, 15, 20, 46, or 392 of the p53 protein.

9. The composition of claim 1, wherein the amount of the antineoplastic drug is suboptimal for the treatment of the cancer without the inhibitor of CRM1.

10. The composition of claim 1, wherein the lung cancer is selected from non-small cell lung cancer at least one of an adenocarcinoma, a squamous cell carcinoma, or a large cell carcinoma.

11. A method of treating a cancer comprising:
identifying a patient with a cancer, wherein the cancer is selected from the group consisting of lung, pancreatic, leukemia, a glioma, cervical, ovarian, an osteosarcoma, multiple myeloma, and a renal cancer; and
providing the patient with an effective amount of a combination of a platinum-based antineoplastic drug and an inhibitor of CRM1, wherein the inhibitor of CRM1 enhances the anti-neoplastic effect of the antineoplastic drug.

12. The method of claim 11, wherein the step of identifying a patient with lung cancer is defined further as comprising obtaining a biopsy from the patient and at least one of determining that the biopsy obtained from the patient is suspected of being cancerous that overexpresses a chromosome maintenance region 1 (CRM1) gene or has a change in a post-translational modification of a p53 protein.

13. The method of claim 11, wherein the antineoplastic drug is a platinum-based antineoplastic drug selected from at least one of cisplatin, carboplatin, oxaliplatin, satraplatin, picoplatin, nedaplatin, triplatin or lipoplatin.

14. The method of claim 11, wherein the antineoplastic drug is a taxane or an inhibitor of epidermal growth factor receptor.

15. The method of claim 11, wherein the inhibitor of CRM1 is at least one of Leptomycin A, Leptomycin B, Leptomycin analogs, an RNA that interferes with CRM1expression or mRNA, ratjadone, valtrate, acetoxychavicol acetate, an oral CRM1 inhibitor (CBS9106), a selective inhibitor of nuclear export (SINE), a natural compound that inhibits CRM1, or curcumin.

16. The method of claim 11, wherein the cancer is defined further as a CRM1 over-expressing cancer.

17. The method of claim 11, wherein the cancer is defined further as having a modified p53 with deregulated p53 activity.

18. The method of claim 11, wherein the cancer is defined further as having post-translationally modified p53, therein the modification is a ribosylation or a phosphorylation.

19. The method of claim 11, wherein the cancer is defined further as having post-translationally modified p53, wherein the modification is a phosphorylation at threonine residue 55, serine residues 9, 15, 20, 46, or 392 of the p53 protein.

20. The method of claim 11, wherein the amount of the antineoplastic drug is suboptimal for the treatment of the cancer without the inhibitor of CRM1.

21. The method of claim 11, wherein the lung cancer is selected from non-small cell lung cancer at least one of an adenocarcinoma, a squamous cell carcinoma, or a large cell carcinoma, or a small cell lung cancer.

22. A composition for treating a lung cancer comprising:
at least one of cisplatin or lipoplatin; and a leptomycin B, wherein the leptomycin B enhances the anti-neoplastic effect of the cisplatin or lipoplatin against lung cancer.

23. The composition of claim 22, wherein the lung cancer is defined further as a chromosome maintenance region 1 (CRM1) expressing lung cancer.

24. The composition of claim 22, wherein the cancer is defined further as having a modified p53 with deregulated p53 activity.

25. The composition of claim 22, wherein the composition further comprises an shRNA that knocks down CRM1 expression.

26. The composition of claim 22, wherein the amount of the cisplatin or lipoplatin is suboptimal for the treatment of lung cancer without the leptomycin B.

27. A method of treating a cancer comprising:
obtaining a biopsy from a patient with a cancer, wherein the cancer is selected from the group consisting of lung, pancreatic, leukemia, a glioma, cervical, ovarian, an osteosarcoma, multiple myeloma and a renal cancer;
determining that a sample of tissue suspected of being cancerous overexpresses a chromosome maintenance region 1 (CRM1) gene or a post-translational modification of a p53 protein; and
providing the patient with an effective amount of a combination of a platinum-based antineoplastic drug and an inhibitor of CRM1, wherein the inhibitor of CRM1 enhances the anti-neoplastic effect of the antineoplastic drug if the patient has an increase in expression of a chromosome maintenance region 1 (CRM1) gene or a change in the post-translational modification of a p53 protein when compared to non-cancerous tissue.

28. The method of claim 27, wherein the antineoplastic drug is a platinum-based antineoplastic drug selected from at least one of cisplatin, carboplatin, oxaliplatin, satraplatin, picoplatin, nedaplatin, triplatin or lipoplatin.

29. The method of claim 27, wherein the antineoplastic drug is a taxane or an inhibitor of epidermal growth factor receptor.

30. The method of claim 27, wherein the inhibitor of CRM1 is at least one of Leptomycin A, Leptomycin B, Leptomycin analogs, an RNA that interferes with CRM1 expression or mRNA, ratjadone, valtrate, acetoxychavicol acetate, an oral CRM1 inhibitor (CBS9106), a selective inhibitor of nuclear export (SINE), a natural compound that inhibits CRM1, or curcumin.

31. The method of claim 27, wherein the cancer is defined further as a CRM1 over-expressing cancer.

32. The method of claim 27, wherein the cancer is defined further as having a modified p53 with deregulated p53 activity.

33. The method of claim 27, wherein the cancer is defined further as having post-translationally modified p53, therein the modification is a ribosylation or a phosphorylation.

34. The method of claim 27, wherein the cancer is defined further as having post-translationally modified p53, wherein the modification is a phosphorylation at threonine residue 55, serine residues 9, 15, 20, 46, or 392 of the p53 protein.

35. The method of claim 27, wherein the amount of the antineoplastic drug is suboptimal for the treatment of the cancer without the inhibitor of CRM1.

36. The method of claim 27, wherein the lung cancer is selected from non-small cell lung cancer at least one of an adenocarcinoma, a squamous cell carcinoma, or a large cell carcinoma, or a small cell lung cancer.

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthetic primer

<400> SEQUENCE: 1
ggtggtctcc tctgacttca aca                                                23

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
gttgctgtag ccaaattcgt t                                                  21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 3
ggaaccagtg cgaaggaata                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tttcgctggt cctacttgct                                                20
```